United States Patent
Tamminen et al.

(10) Patent No.: US 12,391,807 B2
(45) Date of Patent: Aug. 19, 2025

(54) EXTRACTION OF VALUABLE COMPONENTS FROM BARK

(71) Applicant: Teknologian tutkimuskeskus VTT Oy, Espoo (FI)

(72) Inventors: Tarja Tamminen, Espoo (FI); Klaus Niemelä, Espoo (FI); Stina Grönqvist, Espoo (FI); Sami Alakurtti, Espoo (FI); Miikka Ruuskanen, Espoo (FI); Anna Kalliola, Espoo (FI)

(73) Assignee: Teknologian tutkimuskeskus VTT Oy, Espoo (FI)

( * ) Notice: Subject to any disclaimer, the term of this patent is extended or adjusted under 35 U.S.C. 154(b) by 917 days.

(21) Appl. No.: 17/287,145

(22) PCT Filed: Oct. 23, 2019

(86) PCT No.: PCT/FI2019/050756
§ 371 (c)(1),
(2) Date: Apr. 21, 2021

(87) PCT Pub. No.: WO2020/084196
PCT Pub. Date: Apr. 30, 2020

(65) Prior Publication Data
US 2021/0395466 A1 Dec. 23, 2021

(30) Foreign Application Priority Data
Oct. 23, 2018 (FI) .................................. 20185891

(51) Int. Cl.
C08H 7/00 (2011.01)
D21C 1/02 (2006.01)
(Continued)

(52) U.S. Cl.
CPC ................. *C08H 6/00* (2013.01); *D21C 1/02* (2013.01); *D21C 1/04* (2013.01); *D21C 3/02* (2013.01); *D21C 11/0007* (2013.01)

(58) Field of Classification Search
CPC ... C08H 6/00; D21C 1/02; D21C 1/04; D21C 3/02; D21C 11/0007
(Continued)

(56) References Cited

U.S. PATENT DOCUMENTS

836 A 7/1838 Hayes
2,640,052 A 5/1953 Stoddard, Jr.
(Continued)

FOREIGN PATENT DOCUMENTS

CN 1055974 A 11/1991
CN 101223314 A 7/2008
(Continued)

OTHER PUBLICATIONS

Shan et al., CN 103255484 A machine translation in English, Aug. 21, 2013. (Year: 2013).*
(Continued)

*Primary Examiner* — David T Karst
(74) *Attorney, Agent, or Firm* — Laine IP Oy

(57) ABSTRACT

The present invention relates to a process for the extraction of valuable components from a tannin-rich bark raw-material, by carrying out an alkaline cooking step, followed by acid precipitation to separate the valuable components from the remaining bark pulp. The invention also relates to the use of said process on a bark side stream of a chemical pulping plant, whereby the liquor remaining after the extraction of the present process is returned to a stream of the wood pulping process, typically to a black liquor stream, while the spent pulp can be processed further, e.g. by bleaching to give dissolved pulp.

19 Claims, 7 Drawing Sheets

(51) Int. Cl.
*D21C 1/04* (2006.01)
*D21C 3/02* (2006.01)
*D21C 11/00* (2006.01)

(58) Field of Classification Search
USPC .......................................................... 530/500
See application file for complete search history.

(56) References Cited

U.S. PATENT DOCUMENTS

| | | | |
|---|---|---|---|
| 2,781,336 | A | 2/1957 | Zenczak |
| 2,819,295 | A | 1/1958 | Herrick et al. |
| 3,025,250 | A | 3/1962 | Herrick et al. |
| 3,517,052 | A | 6/1970 | Brandts et al. |
| 3,871,893 | A | 3/1975 | Doughty |
| 5,417,888 | A | 5/1995 | Collins et al. |
| 9,828,726 | B2 | 11/2017 | Hiljanen |
| 10,982,032 | B2 | 4/2021 | Morita |
| 2004/0244925 | A1 | 12/2004 | Tarasenko |
| 2011/0297340 | A1 | 12/2011 | Kouisni et al. |
| 2018/0362692 | A1* | 12/2018 | Morita .................. C08F 251/00 |

FOREIGN PATENT DOCUMENTS

| | | | | |
|---|---|---|---|---|
| CN | 102268833 | A | | 12/2011 |
| CN | 102272318 | A | | 12/2011 |
| CN | 102631381 | A | | 8/2012 |
| CN | 102675581 | A | * | 9/2012 ............. C08G 18/64 |
| CN | 103255484 | A | * | 8/2013 ............... D01C 1/02 |
| CN | 108030086 | A | | 5/2018 |
| DE | 102010048614 | A1 | | 4/2012 |
| ES | 8507597 | | | 8/1985 |
| JP | S4719561 | A | | 9/1968 |
| JP | H08500854 | A | | 1/1996 |
| JP | 2017058803 | A | | 3/2017 |
| JP | 2017106160 | A | | 6/2017 |
| WO | WO9213849 | A1 | | 8/1992 |
| WO | WO9315261 | A1 | | 8/1993 |
| WO | WO2017110190 | A1 | | 6/2017 |
| WO | WO2018115290 | A1 | | 6/2018 |

OTHER PUBLICATIONS

Jiang et al., CN 102675581 A machine translation in English, Sep. 19, 2012. (Year: 2012).*

Wang et al., CN 102631381 A machine translation in English used for citation, Aug. 15, 2012. (Year: 2012).*

Feng et al: Selectivity of soda-AQ pulping of kenaf bark. Cellulose Chemistry and Technology, 2003, vol. 36, pp. 367-374.

Fernandes et al: Papermaking potential of wood and pre-hydrolyzed barks of eucalyptus globulus. EWLP 2014, Jun. 24-27, 2014.

Kubota et al: The utilization of Japanese Larch BArk Extract for Wood Adhesives VII. Rinsan Shikenjoho, 1987, vol. 1, pp. 10-17.

Lindgren et al: Techno economic evaluation of lignin extraction in a dissolving pulp biorefinery. NWBC, Mar. 28-30, 2017.

Ruuskanen: The influence of the origin and treatment history of spruce and pine bark on the extraction of tannin. Master's thesis—University of Helsinki, May 2017.

* cited by examiner

EXTRACTION OF VALUABLE COMPONENTS FROM BARK

BACKGROUND OF THE INVENTION

Field of the Invention

The present invention concerns the application of alkaline cooking processes on industrial bark side streams.

Particularly the invention concerns a method for extracting valuable components from tannin-rich bark.

Description of Related Art

Before the pulping process is carried out, the wood raw material is typically subjected to debarking. Since the bark of most wood species has low cellulose content and a relatively high content of components that have a harmful effect on the pulping process, the separation of the bark has been considered advantageous for the overall process.

The remaining bark residues are typically used as energy sources in pulp mills, and the excess is considered to be low-value solid fuel.

The bark of some wood species is, however, rich in valuable components, such as tannins, that could be highly useful when separated from the bark, whereby discarding the bark as waste is not an effective way of utilizing the wood raw material.

Therefore there is a need for a process that would utilize a higher portion of the wood raw material.

It is known that barks differ in content based on their origin, such as wood species and processing history (see e.g. the Master's thesis by Miikka Ruuskanen, 2017).

Extraction of tannins by hot water extraction has been investigated, with the first attempts on extracting bark using alkali solutions carried out a long time ago (see e.g. US 836), but considered to provide only low yields and to have a lack of economic feasibility. Further, tannin extraction leaves other bark constituents, i.e. the main part of bark, unused.

Such an extraction to obtain a tannin fraction has been described in, e.g. ES 537060, which describes an alkali-boosted extraction process, where the obtained extract is used in thermosetting binders and adhesives.

Bark extracts have been used in resin products, such as in U.S. Pat. No. 2,819,295, which describes an alkaline extraction followed by heating to obtain a resin product, as well as in M. Kubota, et al. (1987), which describes the use of bark extracts in preparing resins.

Alkaline cooking of bark has not been under extensive investigation, partly due to the differences in composition between bark and wood (xylem). However, Z. Feng and R. Alen (2003) describes the soda cooking of kenaf bark to produce cellulose pulp. Particularly the conditions of the process were optimized to provide high delignification.

These documents pay attention mainly to the problems that bark introduces to the pulping of wood.

For utilizing the components of the bark, the procedure most extensively investigated in the past is hot water extraction (HWE), but these described procedures have focused mainly on conditions that are not expected to dissolve lignin, such as in soda cooking. The yield of hot water extraction is, in fact, low, whereby purification and concentration by solvent extractions or membrane filtration are needed.

As the above publications show, the first attempts on extracting bark using alkali solutions have been carried out a long time ago. However, only minor fractions of the valuable bark components can be recovered for value-added use by the presently available process concepts.

SUMMARY OF THE INVENTION

The invention is defined by the features of the independent claims. Some specific embodiments are defined in the dependent claims.

According to a first aspect of the present invention, there is provided a process for extraction of valuable components from a tannin-rich bark raw-material.

According to a second aspect of the present invention, there is provided a process for extraction of tannins and lignin from the bark of softwood species, or from the bark of oak, acacia, willows, chestnut or *eucalyptus*.

Particularly, the process is, however, designed to provide means for separating a variety of fractions from bark, including components, such as inorganics, glucose hydrolysates or dissolving pulp, in addition to the polyphenolics, i.e. the tannins and the lignin.

Alkaline cooking extracts a significantly larger proportion of the bark polyphenols than the commonly used hot water extraction. In addition, the polyphenol fraction obtained from soda cooking can be recovered by simple acid precipitation.

Alternatively, alkaline cooking can be performed after hot water extraction (HWE), whereby a first portion of polyphenols can be separated from the bark raw material already before soda cooking. This will increase the total yield of polyphenols, particularly tannin, of the process.

The polyphenolic fraction obtained from the present process (herein named BL tannin) is a potential raw material to replace phenol in general The polyphenol fraction obtained from the present process is a potential raw material for phenol formaldehyde (PF) type resins, containing more reactive site than technical lignins obtained from the soda cooking of the regular debarked roundwood, due to the tannin component.

The native type tannin obtained by the traditional HWE process (herein named HWE tannin) is, traditionally regarded to be more suitable e.g. for tanning of leather.

The polyphenol fraction is expected to contain some suberin-derived hydroxy fatty acids, in addition to the previously mentioned tannin and lignin. These bring additional functionality to the polyphenol fraction.

The structural changes of tannin taking place during the alkaline cooking have been discovered not to be detrimental in respect to its subsequent uses. This is one of the critical findings of the present invention.

Another surprising finding made by the present inventors is that the components of the polyphenol fraction, particularly the tannins, can be recovered using acid precipitation. Previously, these components have been considered to have a too high solubility in water to allow such precipitation.

The present concept has the particular advantage of being possible to integrate to existing pulp mills, especially if the mill has installed a lignin recovery line, since the present process utilizes similar cooking conditions and produces a spent cooking liquor that is suitable for being returned to the chemical recovery system of the wood pulping process.

The present concept also yields a pulp that is suitable for use in various applications, such as for use as a raw material to produce monosugars, for use as a raw material for dissolving pulp after bleaching and for use as a raw material for reinforcement fibres in composites.

In addition, extractives, hydroxyl acids and other valuable components can be recovered from spent cooking liquor.

EMBODIMENTS OF THE INVENTION

Definitions

Figure 1:
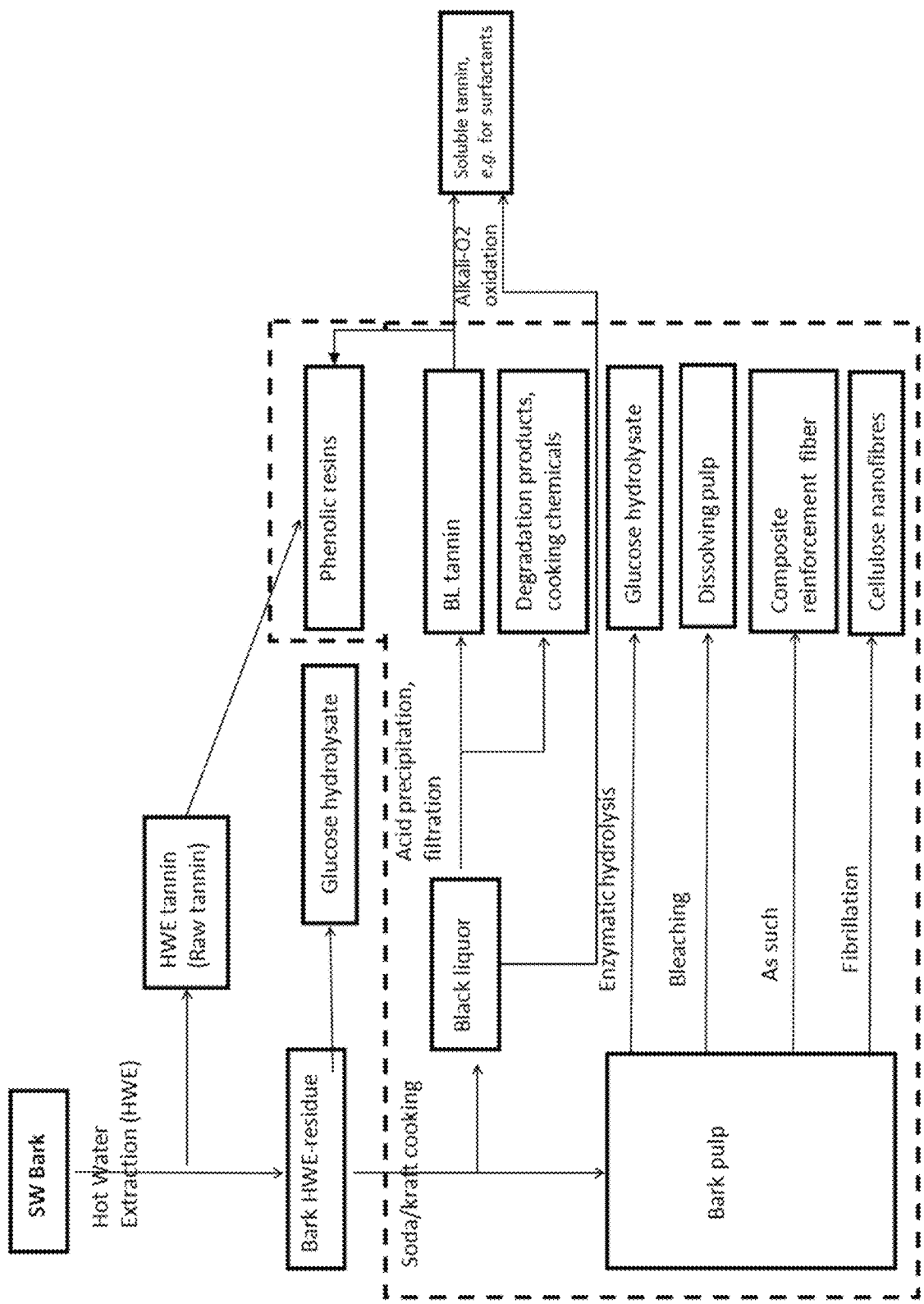
FIG. 1 is a schematic drawing of all the process steps that may be included in the process of a preferred embodiment of the invention.

In the present context, the term "tannin-rich bark" encompasses the bark of certain wood species, these barks having been shown to contain more than 5 w-% of tannins, typically 10-40 w-%.

Such wood species having tannin-rich bark include mangrove and mimosa, both with a typical tannin content in their bark of 30-40 w-%, pine (pinus radiate), with a typical bark tannin content of 10-20 w-%, as well as spruce and oak, both with a typical bark tannin content of 10-15 w-%.

The term "valuable components", in turn, encompasses polyphenols, which in addition to tannins (both condensed and hydrolysable tannins) also include lignin, as well as various extractives and hydroxyl acids, such as stilbenes, flavonoids, lignans, simple phenolics and phenolic acids.

Since tannin and lignin are typically co-extracted, the tannin fractions mentioned in the present context typically contain also some lignin, before further separation.

Specifically, in the present context, two main tannin fractions are discussed. One of these is the "HWE tannin", which is obtained from an optional pre-treatment of the raw material, i.e. from a hot-water extraction (HWE). The other essential tannin fraction discussed herein is the "BL tannin", which is obtained from the cooking of the raw material (BL=black liquor).

The present invention relates to a process for the extraction of valuable components from tannin-rich bark raw-material. This is carried out by alkaline cooking followed by acid precipitation to separate the valuable components from the remaining bark pulp.

The process is particularly suitable for extracting tannins from the bark. However, the lignin will also be separated from the raw material The raw material used in the process of the invention is typically selected from the bark of softwood species, or from the bark of mangrove, mimosa, oak, acacia, willows, chestnut or eucalyptus, softwood bark being preferred due to its availability as well as its high tannin content, combined with a generally suitable composition.

The most preferred softwoods are pine and spruce species.

The bark to be used as raw material is typically obtained in a suitable form directly from pulp mills or other debarking processes. Regardless of the source, the material is typically added to the process in the form of crushed bark chips.

The step of cooking the raw-material is preferably carried out by using a white liquor containing sodium hydroxide (NaOH) and sodium sulfide ($Na_2S$), and by using common kraft cooking conditions, thereby providing a black liquor containing the desired polyphenols (BL tannin), which can be separated from the remaining bark pulp.

According to an embodiment of the invention, the used cooking conditions are: 14-20% effective alkali (EA), 150-178° C., and 60-140 min cooking time. Preferably, the white liquor has an effective alkali content of 16-18%, while a preferred cooking temperature is 160-170° C., and a preferred cooking time is 1 or more hours, more preferably 1.5-2 h.

In order to separate the polyphenol fraction (BL tannin) from the obtained black liquor, an acid precipitation step is carried out after the cooking step. The acid precipitation can be carried out using carbon dioxide, and can optionally include acidifying the black liquor using an acid, such as sulfuric acid ($H_2SO_4$), preferably at a temperature of 60-90° C., more preferably at a temperature of 70-80° C., and to a pH level of 1-4, preferably to pH 2-3.

The product obtained by the acid precipitation is preferably separated from the remaining liquor by filtration, to provide a solid fraction containing the BL tannin, containing also lignin, thus leaving a liquid fraction containing cooking chemicals as well as some degradation products.

The BL tannin fraction typically contains, in addition to the above mentioned tannins and lignin, also some suberin-derived hydroxy fatty acids.

According to an embodiment, this BL tannin fraction is processed further to give phenolic resins. This can be done e.g. by hydroxymethylation using formaldehyde.

According to another embodiment, the BL tannin fraction is oxidized to give a tannin fraction having increased solubility. Oxidation has been previously applied to water insoluble technical lignins as means to convert them water soluble. The oxidation has been found to increase the anionic charge in the lignin. Now the same has been attempted successfully also with the BL tannin described herein.

Unmodified tannins are only soluble in water at alkaline conditions, at a pH value of ≥11. However, oxidation of the tannin has been found to increase the pH range, wherein the tannin is soluble in water, at least to a range of ≥8.

Also hot-water extracted tannin (HWE tannin) has a higher solubility in water, as compared to BL tannin, but the oxidized tannin is more suitable for use, e.g., as a surfactant.

Typically, the oxidation is carried out using oxygen ($O_2$) gas, preferably in high-pressure conditions.

The oxidation can be carried out either directly in the spent cooking liquor (which is an alkaline solution, wherein even the BL tannins are soluble), or after the optional acid precipitation and redissolution in alkali.

The cooking chemicals of the liquid fraction remaining after the acid precipitation, are preferably recycled. Since this remaining cooking liquor is highly similar to the cooking liquor of common cellulose pulping processes, the liquor of the present process can for example be combined with these common liquors.

According to a preferred embodiment of the invention, the soda pulping is preceded by a step pre-treatment of the bark, e.g. by hot-water extraction, to remove, or at least decrease the content of, silicon and ashes. The silicon and ash components are harmful for cellulose pulping processes, as they are difficult to remove once they have been carried to the black liquor. However, in small amounts the process can withstand the presence of these components, whereby the pre-treatment step is not essential.

Thus, the cooking step of the process can be preceded by a hot-water extraction (HWE), wherein the raw material is added to an aqueous solution, and the resulting mixture is heated for 1-5 h at 70-110° C., in order to separate inorganics, and possibly recover a first portion of tannins or other valuable components from the bark raw material.

The thus obtained hot-water extract is preferably separated, e.g. by membrane separation, into an organic fraction, containing mainly a first portion of the tannins, i.e. the HWE tannin fraction, and an inorganic fraction.

According to another preferred embodiment, the optional pre-treatment step can be carried out by washing the raw-material with an aqueous inorganic or organic acid solution, such as a solution of nitric, sulfuric, or hydrochloric acid, e.g. having a concentration of 1-3%, typically about 1%, at an increased temperature, such as a temperature of 30-50° C., preferably about 40° C., and separating the solids from the spent solution. The separation is preferably carried out at a vacuum, suitably in a rotary vacuum drum washer. The obtained separated solids are preferably rinsed with water of the same temperature as used for the acid washing, and pressed, e.g. with a mechanical press, to remove the residual water. Finally, the used acid is typically neutralized, e.g. by using sodium hydroxide (NaOH).

Another option for the pre-treatment is a pre-extraction using $Na_2CO_3$ and urea as extraction chemicals, or using chelating agents, such as EDTA.

As mentioned above, the process continues after the optional pre-treatment with the cooking and acid precipitation of the raw material.

The bark pulp remaining from cooking also contains components that can be of value. Therefore, it is preferred to process also this fraction further.

Thus, according to a preferred embodiment of the present invention, the bark pulp from cooking is processed either by enzymatic hydrolysis, to give a glucose hydrolysate, or by bleaching, to give a dissolving pulp.

A further benefit of the enzymatic hydrolysis, when carried out at this stage of the process, is that the alkaline cooking (with or without preceding HWE) improves the enzymatic hydrolysability of the bark pulp, as the removal of the BL tannin fraction improves the accessibility of the enzymes. This sugar stream is highly suitable for fermentation.

According to a further embodiment of the invention, the bark pulp from the cooking is used as a raw material for the production of cellulose nanofibers (CNF).

The process of the present invention has the benefit of being highly similar to the common wood pulping processes, whereby the present process can be easily applied on the site of these pulp mills.

The present invention thus relates also to the use of this process on a bark side stream of a chemical pulping plant, whereby the bark is obtained from the debarking of the wood material intended to undergo pulping. The bark pulping liquor remaining after the recovery of the BL tannins can also be returned to a stream of the wood pulping process, typically to a black liquor stream.

Suitable applications for the product fractions of the present invention are highly similar to the uses of common solubilized lignins. According to one option, the BL tannin fraction, which contains the tannins and the lignin, can be used to prepare resins, particularly PF resins. This tannin fraction is even more suitable for said purpose than the commonly used lignin fraction obtained from a cellulose pulping process, since the mixture of tannins and lignins of said BL tannin fraction introduce further reactive sites into the mixture.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to one embodiment or an embodiment means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment. Where reference is made to a numerical value using a term such as, for example, about or substantially, the exact numerical value is also disclosed.

As used herein, a plurality of items, structural elements, compositional elements, and/or materials may be presented in a common list for convenience. However, these lists should be construed as though each member of the list is individually identified as a separate and unique member.

Furthermore, the described features, structures, or characteristics may be combined in any suitable manner in one or more embodiments. In this description, numerous specific details are provided to provide a thorough understanding of embodiments of the invention. One skilled in the relevant art will recognize, however, that the invention can be practiced without one or more of the specific details.

While the examples herein are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

EXAMPLES

Example 1—Evaluation and Pre-Treatment of Bark Samples

Pulp mill and sawmill have in the past been compared as process variables, and spruce and pine species have been studied as typical sources of softwood bark. In addition, the effect of drying of the bark has been studied.

The results of this comparison are shown in the Master's thesis by Miikka Ruuskanen, 2017.

As an optional pre-treatment of the bark, hot-water extraction was studied. Spruce pulp mill bark, water (and optional chemicals) were loaded to rotating autoclaves at 90° C. and 10% consistency (50 g bark per batch). Reactor reached targeted extraction temperature (90° C.) after 30 min of heating. One reactor vessel at a time was removed after 90 minutes and cooled under water hose. Extract and insoluble bark cake were separated by filtration under vacuum. Extract was weighted and pH measured. The extract was centrifuged and supernatant containing the dissolved tannin was freeze-dried to obtain dry tannin extract. The insoluble bark cake from filtration was washed with deionized water (2×500 mL), weighted and dry solids content measured.

A set of the tannin extracts (aqueous solutions) and extracted bark samples (representing those listed in Table 1) were analysed by GC/MS for potential low-molar mass tannin fragments, extractives and other apolar low-molar mass compounds. For the analyses, the tannin solutions and wet bark residues were extracted by ether and heptane, respectively. The organic extracts were subjected to GC/MS.

TABLE 1

The carbohydrate composition of extracted bark samples from 90 min extractions analysed after 2-stage acid hydrolysis.

| | | Neutral sugars | | | | | | |
|---|---|---|---|---|---|---|---|---|
| Code | Sample | Rhamnose mg/100 mg | Arabinose mg/100 mg | Galactose mg/100 mg | Glucose mg/100 mg | Xylose mg/100 mg | Mannose mg/100 mg | Fructose mg/100 mg |
| HWE | T = 90° C. Pure water t = 90 min | 0.4 | 4.0 | 2.2 | 31 | 4.1 | 4.2 | <0.1 |
| Chemical extraction | T = 90° C. $Na_2CO_3$ = 1 % Urea = 1 % t = 90 min | 0.4 | 4.0 | 2.0 | 33 | 4.2 | 4.6 | <0.1 |

| | | Neutral sugars | | | Acid sugars | | |
|---|---|---|---|---|---|---|---|
| | | Mono- saccharides tot. mg/100 mg | As Poly- saccharides mg/100 mg | Dry matter % | MeGlcA mg/100 mg | GalA mg/100 mg | GlcA mg/100mg |
| Code | Sample | | | | | | |
| HWE | T = 90° C. Pure water t = 90 min | 46 | 41 | 93.21 | 0.26 | 3.56 | 0.13 |
| Chemical extraction | T = 90° C. $Na_2CO_3$ = 1 % Urea = 1 % t = 90 min | 49 | 44 | 92.78 | 0.27 | 3.23 | 0.10 |

Figure 2:
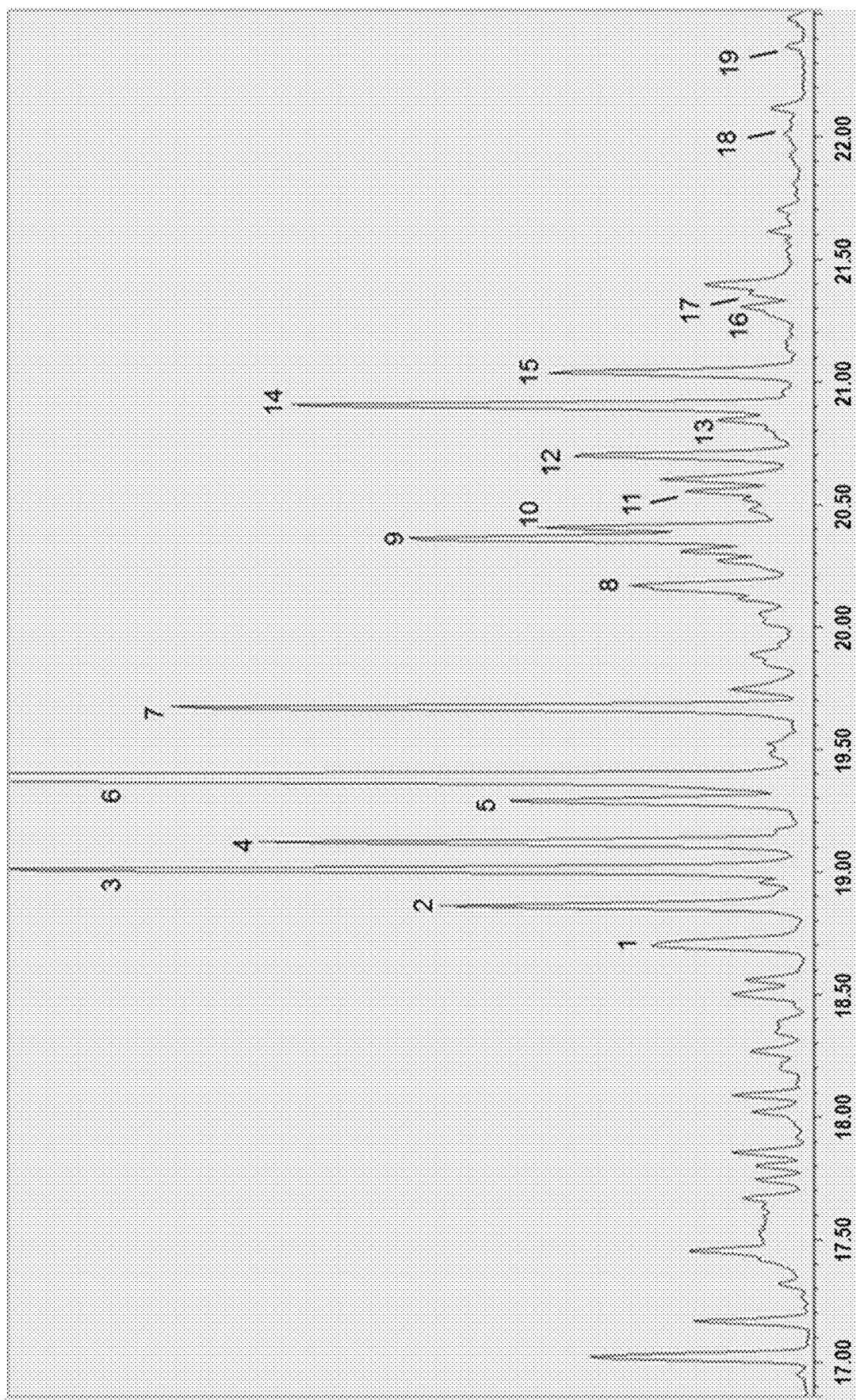
FIG. 2 shows the GC-MS data of some bark extracts, with separation on an RTX-5 column of the trimethylsilylated compounds in a tannin-extracted spruce bark residue, the identified resin acids including: 1 pimaric acid; 2, sandaracopimaric acid; 3, isopimaric acid; 4, palustric acid; 5, levopimaric acid; 6, dehydroabietic acid; 7, abietic acid; 8 and 9, isomeric 7-hydroxydehydroabietic acids; 10, a hydroxyresin acid; 11, 12-hydroxydehydroabietic acid; 12 and 13, hydroxyresin acids; 14, 15-hydroxydehydroabietic acid; 15, 7-oxodehydroabietic acid; 16, an oxoresin acid; 17, a hydroxyresin acid; 18, a dihydroxydehydroabietic acid; and 19, 15-hydroxy-7-oxodehydroaboetic acid, the other peaks in the chromatogram including, among others, fatty acids and neutral diterpenes.

The dominating low-molar mass compounds found in the bark residues (after tannin extraction) were always resin acids; their concentrations seemed to be clearly higher in the spruce-derived than in pine-derived samples. Occasionally, relatively high amounts of oxidised resin acids (especially hydroxydehydroabietic acids) were found in some bark materials (FIG. 2). It is justified to assume that their oxidation has already taken place by autoxidation during the wood or bark storage at the mills. Other compounds usually found in the bark materials included flavonoids, catechins, hydroxystilbenes and other phenolic compounds, such as lignans.

The HWE tannin extracts were also analyzed for their carbohydrate compositions (Table 2).

TABLE 2

Carbohydrate composition of freeze dried extracts (HWE extracted or chemically extracted) after 2-stage sulphuric acid hydrolysis.

| Sample | Description (in mg/100 mg) | Rhamnose | Arabinose | Galactose | Glucose | Xylose | Mannose | Fructose | Mono- saccharides | Poly- saccharides |
|---|---|---|---|---|---|---|---|---|---|---|
| Chemical extraction | T = 90° C. Na$_2$CO$_3$ = 1% Urea = 1% t = 90 min | 2.7 | 6.5 | 6.0 | 12 | 0.6 | 4.3 | 1.4 | 33 | 30 |
| HWE | T = 90° C. Pure water t = 90 min | 1.7 | 2.7 | 3.2 | 9.0 | 0.3 | 2.6 | 1.8 | 21 | 19 |

Both gravimetric and acid soluble lignin were analysed. The methoxyl content of the selected samples was analysed to elucidate the amount of lignin versus tannin in samples. Both lignin and tannin are detected with the Kason lignin method. The non-lignin components can be subtracted from the total amount of components analysed by Kason by comparing the amount of methoxyls found in the Kason lignin sample with the theroretical amount of methoxyls in guaiacyl-type lignin.

The Kason method indicated that the untreated spruce pulp mill bark would contain 40.29% of lignin. However, the detected methoxyl content of the Klason sample was only 4.89%. Thus, it could be concluded that only 34% of the by Klason method analysed lignin was actually lignin and as much as 66% was something else, mainly tannin. Thus the lignin content of this bark was corrected to be 14%. About the same value for lignin content was obtained when the detected amount of methoxyls in the untreated bark sample was divided by the theoretical amount of lignin, i.e. 1.50%/14%=10.7%. This means that all methoxyl groups in the bark are derived from lignin. This is not necessarily true for all bark samples and need to be verified via the gravimetric lignin analysis.

These principles were applied to analyse the lignin and tannin contents of selected bark and extract samples. The tannin content of the original pulp mill bark was measured to be 28% and lignin content 11-12% depending on the calculation method. The tannin content is only slightly reduced by extraction (water or Na$_2$CO$_3$/urea). The extracts contain only minor lignin contamination. However, the content of tannin in the extracts is only 35-39%, the rest probably consisting of ash, carbohydrates and extraction chemicals.

The analyzed lignin and tannin contents in extracts are shown in Table 3, with the elementary composition of the selected samples shown in Table 4.

TABLE 3

Lignin and tannin contents of selected tannin extracts, based on the methoxyl contents.

| Sample | Gravimetric "lignin" (%) | Acid soluble lignin (%) | Methoxyls in extract (%) | Lignin content | Tannin content | Polysaccharides | Ash + extractives + unidentified |
|---|---|---|---|---|---|---|---|
| Spruce tannin, water extracted | 41.58 | 5.4 | 0.24 | 1.75 | 39.8 | 30 | 23.05 |
| Spruce tannin, Na$_2$CO$_3$ and Urea extracted | 34.78 | 4.5 | 0.28 | 1.99 | 32.8 | 30 | 30.71 |

TABLE 4

Elementary composition of the same samples. Normalised values (to 100% organic matter) are given in parenthesis.

| Sample | Nitrogen (%) | Carbon (%) | Hydrogen (%) | Sulphur (%) | Oxygen (%) | Ash as difference (%) |
|---|---|---|---|---|---|---|
| Spruce tannin, water extracted (HWE) | 0.52 (0.58) | 47.59 (52.96) | 5.47 (6.09) | 0 | 36.28 (40.37) | 10.14 |
| Spruce tannin, Na$_2$CO$_3$ and Urea extracted, Chemical extraction | 5.28 (5.29) | 45.65 (51.27) | 5.13 (5.76) | 0 | 32.97 (37.03) | 10.97 |

The chemical composition of freeze-died extracts from 90 min extractions using different extraction chemicals as well as extraction temperature and time was analysed (see Table 1). Only minor differences in the carbohydrate compositions could be detected. The samples were pre-treated by 2-stage acid hydrolysis for the carbohydrate analysis. The carbohydrate content (as polysaccharides) varied between 15 and 30%, depending on the extraction conditions.

The composition of the residue remaining after hot-water extraction was also analyzed (see Tables 5 and 6).

TABLE 5

Elementary composition of selected bark samples. Normalised value (to 100% organic matter) are given in parenthesis.

| Sample | Nitrogen (%) | Carbon (%) | Hydrogen (%) | Sulphur (%) | Oxygen (%) | Ash as difference (%) |
|---|---|---|---|---|---|---|
| Starting bark (spruce) | 0.5 (0.54) | 49.77 (53.40) | 5.6 (6.01) | 0 | 37.33 (40.05) | 6.8 |
| Hot water extracted (HWE) bark | 0.44 (0.46) | 49.71 (52.2) | 5.40 (5.67) | 0 | 39.64 (41.64) | 4.81 |
| Chemically extracted ($Na_2CO_3$ and Urea) bark | 0.45 (0.48) | 48.46 (51.22) | 5.54 (5.86) | 0.44 (0.47) | 39.72 (41.98) | 5.39 |

TABLE 6

Carbohydrate composition of samples of remaining bark after extractions and after 2-stage sulphuric acid hydrolysis.

| | Neutral sugars | | | | | | |
|---|---|---|---|---|---|---|---|
| Sample | Rhamnose mg/100 mg | Arabinose mg/100 mg | Galactose mg/100 mg | Glucose mg/100 mg | Xylose mg/100 mg | Mannose mg/100 mg | Fructose mg/100 mg |
| Hot water extracted (HWE) bark | 0.4 | 4.0 | 2.2 | 31 | 4.1 | 4.2 | <0.1 |
| Chemical extracted ($Na_2CO_3$ + Urea) bark | 0.4 | 4.0 | 2.0 | 33 | 4.2 | 4.6 | <0.1 |

| Neutral sugars | | | Acid sugars | | |
|---|---|---|---|---|---|
| Mono- saccharides tot. mg/100 mg | As Poly- saccharides mg/100 mg | Dry matter % | MeGlcA mg/100 mg | GalA mg/100 mg | GlcA mg/100 mg |
| 46 | 41 | 93.21 | 0.26 | 3.56 | 0.13 |
| 49 | 44 | 92.78 | 0.27 | 3.23 | 0.10 |

The chemical compositions of the selected samples used to evaluate the analysis methods were thus calculated as described above (Table 7).

TABLE 7

Chemical composition of selected bark samples (Methoxyls corrected using vanillic acid)

| Description | Carbohydrates (neutral and acidic), % | Lignin (tot) | Other than lignin as analysed by Klason (tannin), % | Ash, % | Not identified, % |
|---|---|---|---|---|---|
| Spruce bark | 44.24 | 14.8 | 26.6 | 6.8 | 7.6 |
| Chemical extracted ($Na_2CO_3$ and urea) spruce bark | 47.6 | 15.4 | 25.2 | 5.39 | 6.4 |
| Hot water extracted (HWE) spruce bark | 44.97 | 18.7 | 23.8 | 4.81 | 7.7 |

Example 2—Soda/Kraft Cooking

The performance of soda pulping was tested by experiments in 1 L reactors, the same as used for the small scale tannin extractions. Liquor-to-bark ratio was 4 L/kg and temperature ramp time 110-120 min. Soda pulping was conducted for 60, 90 or 120 minutes at 160° C. and 170° C. with an active alkali charge of 20% NaOH on solid matter. In the first set of experiments, the raw material used was the pulp mill spruce bark, pre-extracted using 1% $Na_2CO_3$ and 1% urea as extraction chemicals.

Based on the pre-experiments, conditions 160° C. and 90 min were chosen for the study to compare the different bark origins.

About 100 mL of each black liquor was acidified with 1M HCl to pH 2.5 under constant stirring. The samples were centrifuged at 4750 rpm for 15 min and the supernatants were collected. Then, about 100 mL of acidified water (pH adjusted to 2.5 by HCl) was added to wash the precipitate, followed by centrifugation. This washing step was performed 2 times. The precipitated samples were freeze-dried.

The same bark samples were tested as used in the tannin extraction experiments. The barks were soda cooked both after tannin extraction and directly (control). The precipitated BL tannins were analysed in detail.

The pulp yields and yields of precipitated BL tannins, recovered by black liquor acidification, of some barks from soda cooking are shown in Table 8. The used samples varied based on wood species (spruce and pine), origin (pulp mill or saw mill), conditions (fresh or dry), and optional pre-treatment method (no pre-treatment or hot-water extraction). The obtained tannin yields vary depending on the bark origin, but generally higher yields were obtained from the pulp mill samples. Especially high potential would be to use the pulp mill samples directly to soda cooking, as they were found to be poor raw materials for the HWE tannin extraction.

Spruce bark tannin samples were isolated by alkaline (soda) cooking from the bark either after hot water extraction or directly without pre-extraction, to give BL tannin. Some lignin was co-extracted with the tannin, expected to add to the activity of the fractions towards the formaldehyde reactions, due to increased amount of reactive sites.

TABLE 8

Yields of the fractions obtained by soda cooking of the various bark raw materials.

| Bark species | Bark origin | Fresh/ dried bark | HWE extraction/ no pre-treatment (control) | Sample ID | Pulp yield (%) | Recovered BL tannin (%) |
|---|---|---|---|---|---|---|
| Spruce | pulp mill | fresh | HW-extracted | SPFE | 33.9 | 26.6 |
| Spruce | pulp mill | fresh | control | SPFC | 37.4 | 43.3 |
| Spruce | pulp mill | dried | HW-extracted | SPDE | 36.0 | 30.0 |
| Spruce | pulp mill | dried | control | SPDC | 40.0 | 25.0 |
| Spruce | sawmill | fresh | HW-extracted | SSFE II | 49.4 | 19.3 |
| Spruce | sawmill | fresh | control | SSFC | 26.8 | 17.3 |
| Spruce | sawmill | dried | HW-extracted | SSDE | 30.0 | 13.3 |
| Spruce | sawmill | dried | control | SSDC | 33.7 | 14.2 |
| Pine | pulp mill | fresh | HW-extracted | PPFE | 33.7 | 37.3 |
| Pine | pulp mill | fresh | control | PSFC | 30.2 | 25.0 |
| Pine | pulp mill | dried | HW-extracted | PPDE | 25.3 | 38.0 |
| Pine | pulp mill | dried | control | PPDC | 31.3 | 45.4 |
| Pine | sawmill | fresh | HW-extracted | PSFE | 37.5 | 17.5 |
| Pine | sawmill | fresh | control | PPFC | 27.4 | 36.2 |
| Pine | sawmill | dried | HW-extracted | PSDE | 38.0 | 18.4 |
| Pine | sawmill | dried | control | PSDC | 29.2 | 28.8 |

TABLE 9

Content of dissolved tannin in the soda cooking experiments and the yields of the residual bark, with pulp mill spruce bark used as raw material in the cooking.

| Cooking conditions | BL tannin content in spent liquor (A 280 nm, a = 20 L/g cm) | Yield of residual bark, % |
|---|---|---|
| 160° C., 60 min | 89.3 | 46.1 |
| 160° C., 90 min | 84.1 | 42.9 |
| 160° C., 120 min | 87.8 | 43.1 |
| 170° C., 60 min | 90.3 | 43.8 |
| 170° C., 90 min | 86.8 | 43.3 |
| 170° C., 120 min | 86.1 | 42.8 |

Figure 4:
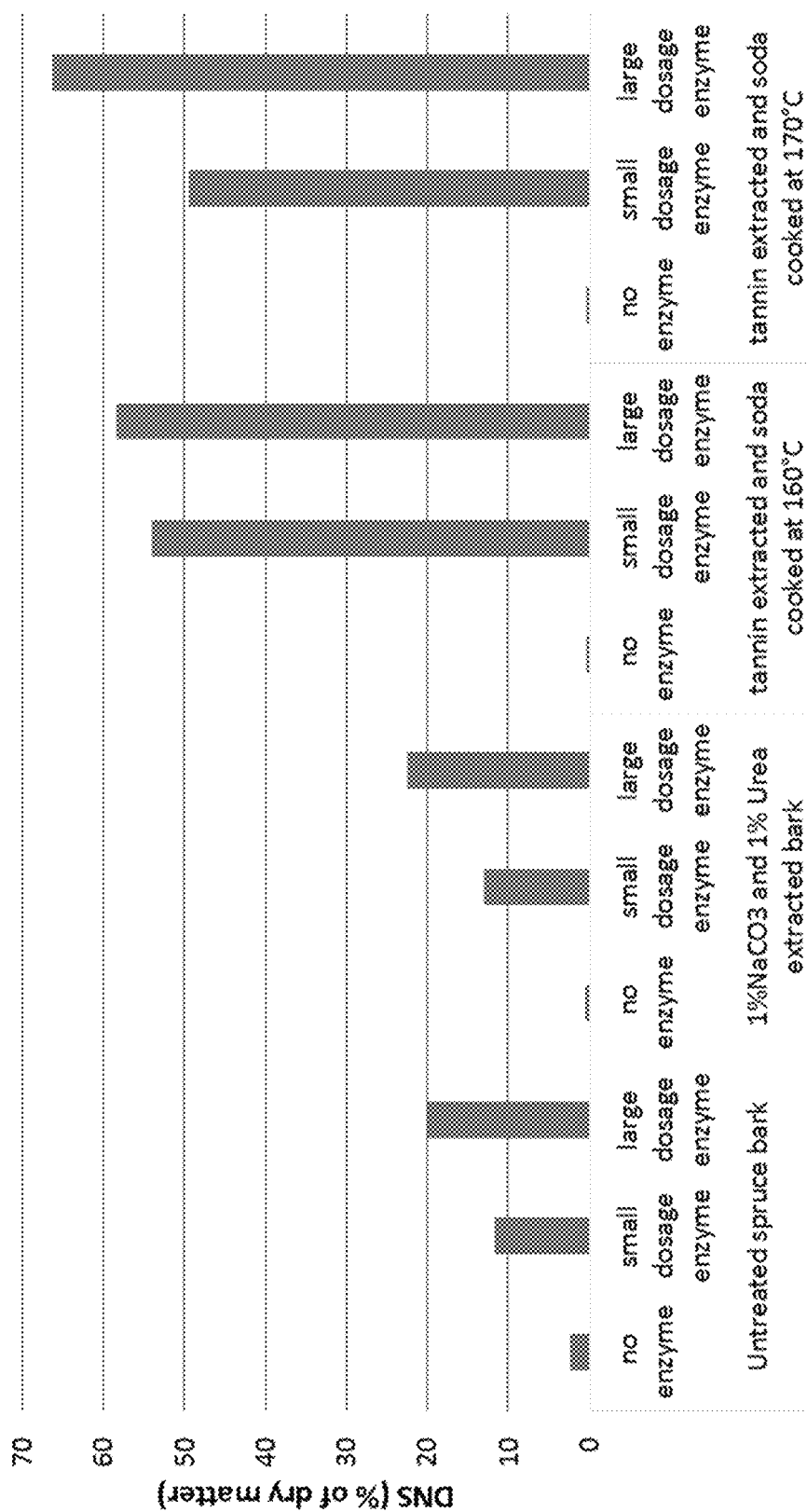
FIG. 4 shows enzymatically hydrolysed carbohydrates from bark residues as analysed by DNS.

For additional information on the reactions of different bark compounds during the soda cooks, a representative selection of 8 pulping spent liquors (black liquors) was analysed by GC/MS. The work covered both polar compounds (typically hydroxy acids) and apolar compounds, recovered by ether extraction. For the analyses of the polar compounds, 0.3-mL liquor samples (after addition of xylitol as the internal standard) were cation-exchanged (to H), filtered, evaporated to dryness and trimethylsilylated. The derivatised samples were subjected to GC/MS. For the analysis of the apolar compounds, 4-mL liquor samples were acidified (after the addition of salicylic and heptadecanoic acids as the internal standards) with 2 M HCl to pH 2-3 and extracted twice with ether. The ether extracts were combined, evaporated to dryness, trimethylsilylated, and analysed by GC/MS as the polar compounds (FIG. 4). The final Example 3—Analysis of the Black Liquor Obtained from the Soda Cooking The performance of the treatment was followed by UV 280 of the spent black liquor. An absorptivity value of 20 L/g cm was used to convert the absorbances into concentrations. The results for six different cooking conditions are given in Table 9. All tested conditions resulted in significant dissolution of lignin-like material and rather similar yields of the residual bark.

identifications were based on the use of an in-house library and extensive literature collections. The indicative concentrations were based on the peak sizes without any corrections.

Figure 3:
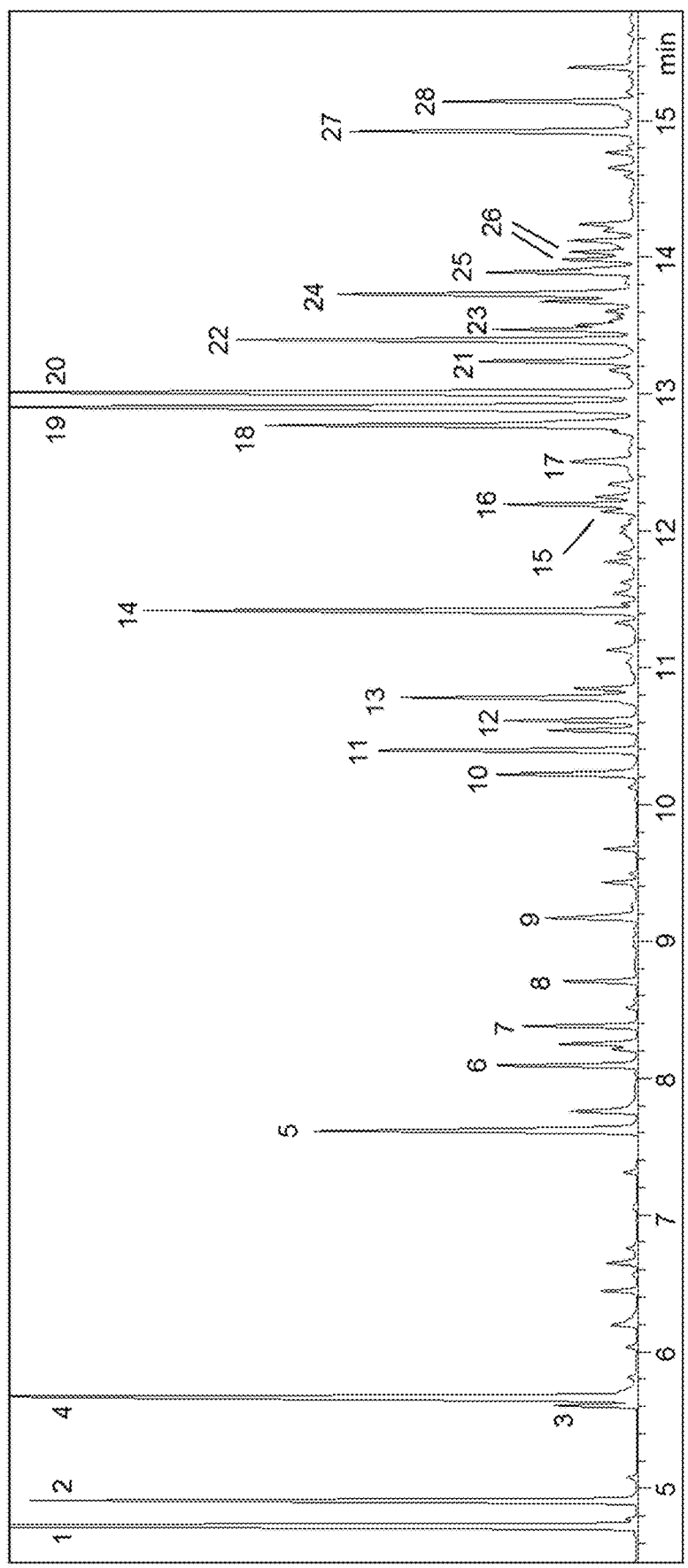
FIG. 3 shows the GC/MS data on cooked samples of bark, with separation on an RTX-5 column of trimetylsilylated polar carboxylic acids from one of the spruce bark soda cooks (SPFC), and selected main compounds including: 1, lactic acid; 2, glycolic acid, 3, 2-hydroxybutanoic acid; 4, oxalic acid; 5, glycerol+phosphoric acid; 6, succinic acid; 7, glyceric acid; 8, C-methyltartronic acid; 9, tartronic acid; 10, citramalic acid; 11, malic acid; 12, 2,5-diydroxypentanoic acid, 13, 3-deoxy-threo-pentonic acid 1,4-lactone; 14, 2-hydroxyglutaric acid; 15, xyloisosaccharinic acid 1,4-lactone; 16, anhydroisosaccharinic acid; 17, 2-hydroxyadipic; 18, α-glucoisosaccharinic acid 1,4-lactone; 19, β-glucoisosaccharinic acid 1,4-lactone; 20, levoglucosan; 21-23, isomeric glucoisosaccharinaric acid lactones; 24-25, isomeric 3-deoxyhexonic acid 1,4-lactones; 26, 2,5-dihydroxyadipic acid (2 isomers); 27, β-glucoisosaccharinaric acid; and 28, α-glucoisosaccharinaric acid, the results further indicating small amounts of several dimer-type compounds eluting at 20-23 min, not shown in the chromatogram.

The same polar compounds (see FIG. 3) were usually found in all the analysed pine and spruce black liquors, although some variation was caused by tree species and material origin (Table 10) (for the identity of the samples, see Table 8). The identifications of the compounds readily reveal that a substantial amount of carbohydrate-derived hydroxy acids are of dicarboxylic acid type (peaks 8-11, 14, 17, 21-23, and 26-28), known to be derived from polyuronates. An additional dicarboxylic acid, oxalic acid (peak 4), is obviously derived from calcium oxalate that is a typical constituent in softwood barks. As the calcium salt, it is not dissolved during the hot water extraction of bark.

TABLE 10

Indicative concentrations (mg/L) of the selected polar carboxylic acids and levoglucosan in the black liquors of selected soda cooks.

| Compound | SSFE | SSFC | SPFE | SPFC | PSFE | PSFC | PPFE | PPFC |
|---|---|---|---|---|---|---|---|---|
| Glycolic acid | 1.88 | 2.13 | 1.65 | 1.69 | 1.97 | 1.39 | 1.52 | 1.57 |
| Lactic acid | 3.13 | 4.82 | 2.69 | 2.59 | 3.14 | 2.74 | 2.06 | 2.13 |
| 2-Hydroxybutanoic acid | 0.58 | 0.56 | 0.29 | 0.21 | 0.28 | 0.27 | 0.10 | 0.10 |
| Glyceric acid | 0.77 | 2.07 | 0.25 | 0.25 | 0.33 | 0.49 | 0.24 | 0.80 |
| 2,5-Dihydroxypentanoic acid | 0.63 | 0.56 | 0.83 | 0.99 | 1.17 | 0.58 | 0.30 | 0.21 |
| 3-Deoxypentonic acids (2) | 1.69 | 1.69 | 1.53 | 1.32 | 2.30 | 1.71 | 1.42 | 1.05 |
| 3-Deoxyhexonic acids (4) | 1.93 | 2.63 | 1.41 | 1.27 | 1.41 | 1.17 | 1.22 | 1.08 |
| Xyloisosaccharinic acid | 0.14 | 0.31 | 0.21 | 0.21 | 0.33 | 0.18 | 0.07 | 0.07 |
| α-Glucoisosaccharinic acid | 1.83 | 2.76 | 2.07 | 1.73 | 1.50 | 1.12 | 1.08 | 0.87 |
| β-Glucoisosaccharinic acid | 3.18 | 4.38 | 3.18 | 3.17 | 3.33 | 2.43 | 2.03 | 1.74 |
| Anhydroisosaccharinic acid | 0.53 | 1.00 | 0.41 | 0.41 | 0.42 | 0.40 | 0.34 | 0.31 |
| Oxalic acid | 2.75 | 1.75 | 2.15 | 1.93 | 1.92 | 1.30 | 2.10 | 1.81 |
| Succinic acid | 0.53 | 0.31 | 0.25 | 0.41 | 0.52 | 0.36 | 0.41 | 0.35 |
| Tartronic acid | 0.67 | 0.63 | 0.25 | 0.37 | 0.19 | 0.27 | 0.30 | 0.91 |
| C-Methyltartronic acid | 0.24 | 0.31 | 0.21 | 0.21 | 0.19 | 0.18 | 0.14 | 0.14 |
| Malic acid | 0.92 | 1.00 | 0.74 | 0.70 | 0.66 | 0.63 | 0.14 | 0.42 |
| Citramalic acid | 0.63 | 0.56 | 0.50 | 0.33 | 0.23 | 0.22 | 0.10 | 0.14 |
| 2-Hydroxyglutaric acid | 1.54 | 1.63 | 1.41 | 1.44 | 1.36 | 1.03 | 0.81 | 0.80 |
| 2,5-Dihydroxyadipic acids (2) | 0.58 | 1.13 | 0.54 | 0.41 | 0.56 | 0.40 | 0.30 | 0.28 |
| α-Glucoisosaccharinaric acid | 1.35 | 1.38 | 1.32 | 1.11 | 1.12 | 0.76 | 0.64 | 0.35 |
| β-Glucoisosaccharinaric acid | 2.80 | 3.01 | 2.90 | 2.10 | 2.20 | 2.02 | 1.46 | 0.94 |
| Levoglucosan | 2.51 | 5.26 | 2.69 | 2.30 | 1.41 | 1.39 | 0.37 | 0.77 |
| Total (g/l) | 30.80 | 39.89 | 27.46 | 25.11 | 26.52 | 21.09 | 17.16 | 16.85 |

Other interesting findings were also made, including the formation of very small amounts of pentose-specific products (peaks 3 and 15). More dominating products were those derived specifically from hexoses (peaks 12-13, 16, and 18-19). The most simple hydroxy acids (peaks 1-2) can be derived from any carbohydrate and thus reveal very little specific information.

The GC/MS analysis of the apolar compounds resulted in the detection, in varying amounts, of up to 150 different compounds that have not yet been fully identified. It has so far become clear, however, that in each black liquor there are degradation or hydrolysis products of polysaccharides, lignin, tannins, and suberin, in addition to fatty and resin acids and other extractives. Interestingly, the tannin-derived catechol derivatives were always more abundant than the monomeric lignin fragments.

Example 4—Analysis of the Pulp Remaining after the Soda Cooking

The chemical composition of the bark samples extracted with 1% $Na_2CO_3$ and 1% urea and thereafter soda cooked was analysed. The methoxyl content of the Klason lignin samples was used to correct the lignin content as described above. The analysis revealed that the soda cooking resulted in enriched carbohydrate composition (Table 11). The results revealed that the carbohydrate content was only slightly enriched by the extraction step, while soda pulping had a more pronounced effect and the carbohydrate content of the samples was found to be as high as 65%. The Soda pulping conditions were not found to affect the carbohydrate yields significantly. Soda cooking dissolved all remaining tannin from the bark, while significant amount of lignin remained in the residue even after soda cooking.

TABLE 11

Chemical composition of starting bark, and 1% $Na_2CO_3$ and 1% urea extracted and soda cooked bark pulp samples.

| Description | Carbohydrates (neutral and acidic), % | Lignin (tot), % | Tannin, % | Ash, % | Unidentif., % |
|---|---|---|---|---|---|
| Spruce bark | 44.24 | 15.1 | 26.2 | 6.8 | 7.6 |
| 1% $Na_2CO_3$ and 1% urea extracted bark, soda cooked at 160° for 120 min | 65.0 | 24.5 | 0.0 | n.a | 10.5 |
| 1% $Na_2CO_3$ and 1% urea extracted bark, soda cooked at 170° for 120 min | 65.0 | 21.5 | 0.6 | n.a | 12.9 |

The overall enrichment of carbohydrates and especially glucanes is clear from the carbohydrate composition analyses in Table 12.

TABLE 12

Carbohydrate composition of the barks after tannin extraction and soda cooking.

| Sample | Rhamnose | Arabinose | Galactose | Glucose | Xylose | Mannose | Fructose | Mono-sacchar. tot. | As Poly-saccharides |
|---|---|---|---|---|---|---|---|---|---|
| | mg/100 mg | mg/100 mg | mg/100 mg | mg/100 mg | mg/100 mg | mg/100 mg | mg/100 mg | mg/100 mg | mg/100 mg |
| Extracted bark (1% Na$_2$CO$_3$ and 1% urea) | 0.51 | 3.81 | 2.22 | 32.9 | 3.80 | 4.64 | <0.1 | 48.0 | 43 |
| Cooked (160° C., 120 min) | <0.1 | 1.2 | 1 | 60 | 7.3 | 2.4 | <0.1 | 72 | 65 |
| Cooked (170° C., 120 min) | <0.1 | 1.1 | 0.9 | 61 | 7 | 2.3 | <0.1 | 72 | 65 |

Example 5—Acid Precipitation

Samples (120 g) of selected black liquors (BL), having been obtained using varying cooking conditions (see Table 13) were acidified using 1M HCl to precipitate the dissolved tannins (and lignins) in a BL tannin fraction. The precipitated samples were freeze-dried and the solids recovered. The yields were as shown in the same Table 13. As shown in these results, the cooking time thus had only minor effect on the absolute yield, the higher temperature increased the yield somewhat. The difference was more clear when comparing the precipitation yields, which clearly increased as a function of cooking time and severity.

TABLE 13

Selected samples, identified based on the used cooking conditions, and the BL tannin yield and characteristics of BL tannins obtained after acidification

| Used cooking conditions | BL tannin yield | Yield (%) of precipitated BL tannin from bark and recovery (%) of the BL tannin from black liquor | BL tannin (%) | Carbo-hydrates (%) | Mw/Mn |
|---|---|---|---|---|---|
| 160° C., 60 min | 7.07 g | 29.5% and 66% | 78.1 | 7.5 | 2923/1860 |
| 160° C., 90 min | 7.18 g | 29.5% and 71% | 74.9 | 7.5 | 2631/1675 |
| 160° C., 120 min | 7.74 g | 32.3% and 73.4% | 70.2 | 7.8 | 2458/1460 |
| 170° C, 120 min | 8.55 g | 35.6% and 82.8% | | | 2921/1612 |

Some further BL tannin samples were then selected (see Table 14) and analyzed to determine their suitability for use in phenol formaldehyde resins.

Example 6. Reactivity of BL Tannin with Formaldehyde $^{31}$P NMR analyses were carried out to determine the frequency of reactive sites (free C3/5 positions) and alkali consuming sites (phenolic hydroxyls and carboxylic acids) of the samples to aid the design of the reagent charges for hydroxymethylation (Table 14).

TABLE 14

Amounts of different hydroxyl group species (mmol/g) in the BL tannin samples.
Reactive and alkali consuming sites were calculated by the equation:
Reactive sites: Guaiacyl + 3 * catechols + 2 * p-OH
Alkali consuming sites: Carboxylic acid + Condensed + Guaiacyl + 2 * catechols + p-OH

| | Raw material | Cooking conditions | Aliph. OH | Carbox. acid | Condensed + Syringyl | Guaiacyl | Catechols |
|---|---|---|---|---|---|---|---|
| Soda cooking scale-up | Spruce bark, sawmill, fresh, HW-extracted | Soda cooking, 90 min, 160° C. | 1.87 | 1.14 | 1.06 | 0.68 | 0.99 |
| | Spruce bark, sawmill, fresh, HW-extracted | Soda cooking, 90 min, 160° C. | 1.84 | 1.21 | 1.20 | 0.74 | 1.05 |
| | Spruce bark, sawmill, fresh, HW-extracted | Soda cooking, 90 min, 160° C. | 2.00 | 1.09 | 1.15 | 0.71 | 1.24 |
| Soda cooking, different spruce barks | Spruce bark, pulpmill, fresh, HW-extracted | Soda cooking, 90 min, 160° C. | 2.13 | 1.35 | 1.01 | 0.82 | 0.85 |
| | Spruce bark, pulpmill, dried, HW-extracted | Soda cooking, 90 min, 160° C. | 2.13 | 1.49 | 1.03 | 0.92 | 0.93 |
| | Spruce bark, pulpmill, fresh, control | Soda cooking, 90 min, 160° C. | 2.27 | 1.27 | 0.85 | 0.63 | 0.75 |

TABLE 14-continued

Amounts of different hydroxyl group species (mmol/g) in the BL tannin samples.
Reactive and alkali consuming sites were calculated by the equation:
Reactive sites: Guaiacyl + 3 * catechols + 2 * p-OH
Alkali consuming sites: Carboxylic acid + Condensed + Guaiacyl + 2 * catechols + p-OH

|  | Raw material | Conditions |  |  |  |  |  |
|---|---|---|---|---|---|---|---|
|  | Spruce bark, pulpmill, dried, control | Soda cooking, 90 min, 160° C. | 2.23 | 1.39 | 1.04 | 0.89 | 0.92 |
|  | Spruce bark, sawmill, fresh, HW-extracted | Soda cooking, 90 min, 160° C. | 2.93 | 1.20 | 1.05 | 0.75 | 0.72 |
|  | Spruce bark, sawmill, dried, HW-extracted | Soda cooking, 90 min, 160° C. | 1.87 | 1.27 | 0.89 | 0.91 | 0.76 |
|  | Spruce bark, sawmill, fresh, control | Soda cooking, 90 min, 160° C. | 2.38 | 1.08 | 0.79 | 0.81 | 0.84 |
|  | Spruce bark, sawmill, dried, control | Soda cooking, 90 min, 160° C. | 2.94 | 1.16 | 1.09 | 0.98 | 0.96 |
| Soda and kraft cooking of spruce barks with varying cooking conditions | Spruce bark, pulp mill, dried, control | Soda cooking, 60 min, 160° C. | 2.27 | 1.37 | 1.35 | 0.78 | 1.20 |
|  | Spruce bark, pulp mill, dried, control | Soda cooking, 90 min, 160° C. | 2.09 | 1.32 | 1.40 | 0.76 | 1.24 |
|  | Spruce bark, pulp mill, dried, control | Soda cooking, 120 min, 160° C. | 2.05 | 1.38 | 1.45 | 0.74 | 1.29 |
|  | Spruce bark, pulp mill, dried, control | Kraft cooking, 60 min, 160° C. | 2.02 | 1.20 | 1.53 | 0.94 | 1.21 |
|  | Spruce bark, pulp mill, dried, control | Kraft cooking, 90 min, 160° C. | 2.03 | 1.23 | 1.61 | 0.92 | 1.19 |
|  | Spruce bark, pulp mill, dried, control | Kraft cooking, 120 min, 160° C. | 1.90 | 1.22 | 1.54 | 0.88 | 1.25 |

|  | Raw material | p-OH-phenyl | Phenolic OH | Total OH | BL tannin purity | Alkali consuming sites | Reactive sites |
|---|---|---|---|---|---|---|---|
| Soda cooking scale-up | Spruce bark, sawmill, fresh, HW-extracted | 1.05 | 3.77 | 6.78 | 1 | 5.91 | 5.75 |
|  | Spruce bark, sawmill, fresh, HW-extracted | 1.14 | 4.13 | 7.18 | 1 | 6.39 | 6.17 |
|  | Spruce bark, sawmill, fresh, HW-extracted | 1.29 | 4.39 | 7.48 | 1 | 6.72 | 7.01 |
| Soda cooking, different spruce barks | Spruce bark, pulpmill, fresh, HW-extracted | 0.91 | 3.59 | 7.06 | 1 | 5.79 | 5.19 |
|  | Spruce bark, pulpmill, dried, HW-extracted | 0.95 | 3.82 | 7.38 | 1 | 6.25 | 5.61 |
|  | Spruce bark, pulpmill, fresh, control | 0.72 | 2.95 | 6.48 | 1 | 4.97 | 4.32 |
|  | Spruce bark, pulpmill, dried, control | 0.84 | 3.68 | 7.31 | 1 | 6.00 | 5.33 |
|  | Spruce bark, sawmill, fresh, HW-extracted | 0.73 | 3.25 | 7.38 | 1 | 5.17 | 4.37 |
|  | Spruce bark, sawmill, dried, HW-extracted | 1.01 | 3.57 | 6.93 | 1 | 5.60 | 5.21 |
|  | Spruce bark, sawmill, fresh, control | 1.06 | 3.50 | 6.96 | 1 | 5.42 | 5.45 |
|  | Spruce bark, sawmill, dried, control | 1.20 | 4.23 | 8.33 | 1 | 6.35 | 6.26 |
| Soda and kraft cooking of spruce barks with varying cooking conditions | Spruce bark, pulp mill, dried, control | 1.33 | 4.66 | 8.30 | 1 | 7.23 | 7.04 |
|  | Spruce bark, pulp mill, dried, control | 1.27 | 4.67 | 8.09 | 1 | 7.23 | 7.02 |
|  | Spruce bark, pulp mill, dried, control | 1.30 | 4.78 | 8.21 | 1 | 7.45 | 7.21 |
|  | Spruce bark, pulp mill, dried, control | 1.24 | 4.92 | 8.14 | 1 | 7.33 | 7.05 |
|  | Spruce bark, pulp mill, dried, control | 1.25 | 4.97 | 8.22 | 1 | 7.39 | 6.99 |
|  | Spruce bark, pulp mill, dried, control | 1.23 | 4.89 | 8.01 | 1 | 7.37 | 7.09 |

There was some variation between the samples depending on the bark history, but the differences were not consistent between the series.

The BL tannins were hydroxymethylated to determine their formaldehyde consumption. The hydroxymethylation reactions were carried out in Radley's reactor with 100 ml flasks with continuous stirring with a mixer blade (for the first 3 samples of Table 14) or in oil bath with 10 ml vials stirring with small magnets (rest of the samples). NaOH (40 M) was added 0.65 eq for alkali consuming sites of the BL tannin. NaOH was added 19.2, 20.8 and 21.8 mmol for samples for first three samples, respectively. In addition, formaldehyde was added 10 mmol for 1 g of BL tannin. This was in excess in relation to the theoretically reactive sites, shown in Table 14. Dry solids content was 10% in hydroxymethylation.

Starting pH of the BL tannin/alkali mixtures varied between 12.0-12.5. The mixtures were stirred at 60° C. overnight to ensure that BL tannin and alkali were fully dissolved. After overnight stirring, the pH values of the mixtures varied between 9.5-10.0.

Formaldehyde was added to the mixture as 37.5 w-% formalin solution. Formalin was added slowly during 10 minutes. Samples at two time points were collected for said first three samples of Table 14, at 60 min and 240 min (last time point). Formaldehyde content of the samples was analyzed with GC (gas chromatography) after hydroxymethylation. When reaction time was longer (240 min) more formaldehyde was consumed. Based on this information, only the last 240 min time points were studied with the rest of the BL tannin samples. Formaldehyde consumptions of the BL tannins are presented in Table 15. In most cases, the actual consumption at 240 minutes corresponded to 50-60% of the theoretically determined sites.

tannin), 0.65 eq alkali, formaldehyde (2:1 to phenol) and 1/3 water were added to the reaction, the soft particles were mainly dissolved. The mixture was stirred mechanically 30 min at 60° C., where after the temperature was increased to 90° C. The target viscosity (3.5-4.5 P) was reached after 2.5 h. The reaction was then stopped and the sample cooled on ice bath. Final pH values ranged between 10.3-11.0 for three separate experiments using BL tannin precipitated from spruce bark alkaline cooking.

The amounts of free formaldehyde in the samples above mentioned samples were 0.12, 0.09 and 0.12%. Thus, for all three samples almost all formaldehyde reacted with BL tannin and phenol. The amounts of free phenol in the

TABLE 15

Formaldehyde consumption in hydroxymethylation. All samples were as shown in Table 14, having been obtained from the spruce bark from either a pulp mill (PM) or a saw mill (SM), and subjected to either soda cooking (SC) or kraft cooking (KC), although here also hydroxymethylated, with the first three samples of Table 14 used in dual tests, at different time points.

| Cooking conditions | Time point (min) | Lignin (g) | NaOH (40M) added (mmol) | NaOH (40M) added (g) | Formalin added (ml) | Formaldehyde in sample before hydroxymethylation (%) | Formaldehyde in sample after hydroxymethylation (%) | Formaldehyde consumption |
|---|---|---|---|---|---|---|---|---|
| Samples from soda cooking (SC) scale up | | | | | | | | |
| Sc, 90 min, 160° C. | 240 | 5.0 | 19.21 | 0.77 | 3.72 | 2.069 | 1.36 | 3.23 |
| Sc, 90 min, 160° C. | 60 | 5.0 | 20.77 | 0.83 | 3.72 | 2.051 | 1.46 | 2.69 |
| Sc, 90 min, 160° C. | 240 | 5.0 | 20.77 | 0.83 | 3.72 | 2.051 | 1.24 | 4.15 |
| Sc, 90 min, 160° C. | 60 | 5.0 | 21.84 | 0.87 | 3.72 | 2.039 | 1.32 | 3.63 |
| Sc, 90 min, 160° C. | 240 | 5.0 | 21.84 | 0.87 | 3.72 | 2.039 | 1.21 | 4.12 |
| Soda cooking (SC) of different barks (PM: pulp mill/SM: saw mill) | | | | | | | | |
| PM: Sc, 90 min, 160° C. | 240 | 0.5 | 1.88 | 0.075 | 0.37 | 2.061 | 1.68 | 1.848 |
| PM: Sc, 90 min, 160° C. | 240 | 0.5 | 2.03 | 0.081 | 0.37 | 2.044 | 1.64 | 1.977 |
| PM: Sc, 90 min, 160° C. | 240 | 0.5 | 1.62 | 0.065 | 0.37 | 2.091 | 1.82 | 1.296 |
| SM: SC, 90 min, 160° C. | 240 | 0.5 | 1.82 | 0.073 | 0.37 | 2.068 | 1.8 | 1.295 |
| SM: SC, 90 min, 160° C. | 240 | 0.5 | 1.76 | 0.070 | 0.37 | 2.074 | 1.57 | 2.431 |
| SM: SC, 90 min, 160° C. | 240 | 0.5 | 2.06 | 0.083 | 0.37 | 2.041 | 1.37 | 3.286 |
| Samples from soda cooking (SC) and kraft cooking (KC) | | | | | | | | |
| Sc, 60 min, 160° C. | 240 | 0.5 | 2.35 | 0.094 | 0.37 | 2.01 | 1.16 | 4.20 |
| Sc, 90 min, 160° C. | 240 | 0.5 | 2.35 | 0.094 | 0.37 | 2.01 | 1.11 | 4.48 |
| Sc, 120 min, 160° C. | 240 | 0.5 | 2.42 | 0.097 | 0.37 | 2.00 | 1.23 | 3.87 |
| KC, 60 min, 160° C. | 240 | 0.5 | 2.38 | 0.095 | 0.37 | 2.01 | 1.22 | 3.91 |
| KC, 90 min, 160° C. | 240 | 0.5 | 2.40 | 0.096 | 0.37 | 2.00 | 1.26 | 3.72 |
| KC, 120 min, 160° C. | 240 | 0.5 | 2.40 | 0.096 | 0.37 | 2.00 | 1.15 | 4.27 |

Example 7. BL Tannin Phenol Formaldehyde Resin Synthesis

BL tannin, alkali (0.65 eq) and water (2/3) are added to the reactor and formaldehyde is added during 10 minutes (charged according to predetermined consumption) without delay. Hydroxymethylation time is 0.5 h at 60° C. The BL tannin mixture and formaldehyde reacted aggressively and formed some soft precipitate. When phenol (1:1 to BL samples were 3.3, 3.9 and 2.3%, also being at acceptable levels. The average (Mw) molar mass values of the resins ranged between 4740 to 5140 g/mol.

Bonding strength of the samples were tested with Automated Bonding Evaluation System (ABES) machine. Pressing temperature was set to 150° C. and pressing times were 45, 90, 180, 300 and 480 s. BL tannin PF resins (50% phenol replaced) displayed 5.2-6.0 N/mm2 shear strength values.

Example 8—Enzymatic Hydrolysis

The possibility to enzymatically hydrolyse bark as such and after tannin extraction and further after soda cooking was evaluated. Experiments were carried out in triplicates in test tubes at 2% consistency (a 100 mg oven dry bark), at 45° C. and pH 5.0 (50 mM sodium acetate buffer) for 48 h with magnetic mixing. The hydrolysis experiments were carried out with combinations of different dosages of commercial cellulase, b-glucosidase and pectinase products (Table 16). Cellulase Celluclast 1.5 L was dosed 10 FPU/g (low dosage) or 25 FPU/g (high dosage), b-glucosidase Novozym 188 was dosed 200 nkat/g (low dosage) or 500 nkat/g (high dosage) and pectinase Pectinex Ultra SP-L was dosed 0 or 5000 nkat/g (high dosage). The enzymatic reactions were stopped by boiling the samples for 10 minutes. Hydrolysis yield was analysed by measuring reducing sugars with 3,5-dinitrosalicylic acid (DNS) method.

TABLE 16

Enzymes used in the hydrolysis studies of spruce bark residues.

| Commercial name | Main enzyme activity | Producer |
| --- | --- | --- |
| Celluclast 1.5 L | Cellulase | Novozymes, Denmark |
| Novozyme 188 | β-glucosidase | Novozymes, Denmark |
| Pectinex Ultra SP-L | Polygalacturonase | Sigma-Aldrich, Denmark |

The hydrolysis yields obtained for both extracted and soda pulped bark samples were significantly higher than those obtained for the untreated bark sample and extracted bark sample (FIG. 4). Increased pulping temperature resulted in higher hydrolysis yields, i.e. 58 and 66% after pulping at 160° C. and 170° C., respectively

Example 9—Bleaching

As another option to hydrolysis, the pulp was bleached by sequence O1-O2-HCE-SDDJ-D0-E1-D1n-D2-A. This consists of two-stage oxygen delignification, hot alkali extraction (HCE) for SiO2 removal, fines removal by super DDJ, Chlorine dioxide bleaching and finally acid stage for metal removal.

The results are listed in the tables below. Table 17 shows that polysaccharides are enriched in pulping and bleaching, but the content of polyphenols (lignin and tannin) remains high. Kappa number is not a reliable measure for lignin content for bark samples. Also ash content is high and it may artificially increase the determined lignin content to some extent.

TABLE 17

Overall composition of the pulps

|  | BARK | SODA BARK | SODA BARK (bleached) |
| --- | --- | --- | --- |
| Extractives (heptane), % |  | 0.2 |  |
| Gravimetric lignin, % |  | 31.5 | 10.6 |
| Acid soluble lignin, % |  | 0.2 | 0.2 |
| Total lignin (polyphenols), % | 42.5 | 31.7 | 10.8 |
| Polysaccharides, % | 45.0 | 59.3 | 71.6 |
| Ash (525 C), % | 4.8 | 9.2 | 1.6 |
| Total, % |  | 100.4 | 94.8 |
| kappa number |  | 59.6 | 0.7 |
| lignin from kappa number, % |  | 8.94 | 0.1 |
| lignin content, if all ash is in lignin, % |  | 22.5 | 9.2 |

Table 18 shows the composition of the polysaccharide fraction after pulping and bleaching relative to the whole sample and normalised to 100%. Glucose (from cellulose and other glucans) is highly enriched in pulping and further in bleaching.

TABLE 18

Carbohydrate composition of the pulps

|  | Rha, mg/100 mg | Ara, mg/100 mg | Gal, mg/100 mg | Glc, mg/100 mg | Xyl, mg/100 mg | Man, mg/100 mg | Fru, mg/100 mg | Mono, tot, mg/100 mg | Poly, tot, mg/100 mg | Non-poly-sacchar., mg/100 mg |
| --- | --- | --- | --- | --- | --- | --- | --- | --- | --- | --- |
| SODA BARK | <0.1 | 0.5 | 0.6 | 57.4 | 4.5 | 3.0 | <0.1 | 66.0 | 59.3 | 40.7 |
| SODA BARK (bleached) | <0.1 | 0.2 | 0.3 | 71.2 | 4.5 | 3.3 | <0.1 | 79.7 | 71.6 | 28.4 |

|  | Rha, % | Ara, % | Gal, % | Glc, % | Xyl, % | Man, % | Fru, % | Mono-sacchar., % |
| --- | --- | --- | --- | --- | --- | --- | --- | --- |
| SODA BARK |  | 0.8 | 1.0 | 86.9 | 6.8 | 4.5 |  | 100 |
| SODA BARK (bleached) |  | 0.3 | 0.4 | 89.3 | 5.6 | 4.2 |  | 100 |

Total ash content is high especially after pulping (Table 19). Especially Fe and Si remain even after bleaching and Si removal.

TABLE 19

Ash content and metal composition of the pulps

| | Ash (525° C.), % | Ca, mg/kg | Co, mg/kg | Cu, mg/kg | Fe, mg/kg | Mg, mg/kg | Mn, mg/kg | Si, mg/kg | tot, mg/kg | tot, % |
|---|---|---|---|---|---|---|---|---|---|---|
| SODA BARK | 9.2 | 4960 | 2.5 | 45.2 | 1500 | 863 | 272 | 2490 | 10132.7 | 1.01 |
| SODA BARK (bleached) | 1.6 | 18.7 | <0.5 | <0.5 | 84.2 | 9.2 | 1.2 | 164 | 277.3 | 0.03 |

As seen in Table 20, the brightness of the bleached pulp was 81 (not full brightness), viscosity 400 mL/G (acceptable) and the Fock number was 93.8%, which indicates very good reactivity in the viscose process. As no general test method for dissolving pulps exists, the Fock number is used as a test method for the applicability as dissolving pulp.

Yield over the bleaching stages was 53%, which is lower than in normal wood pulp bleaching. However, only one preliminary experiment was done without any optimisation.

TABLE 20

Basic pulp characteristics and Fock number of the bleached pulp.

| | kappa number | Brightness, % | Viscosity, mL/g | Yield, % | Fock reactivity % |
|---|---|---|---|---|---|
| SODA BARK | 59.6 | 11.5 | 350 | 40 | 93.8 |
| SODA BARK (bleached) | 0.69 | 81.1 | 400 | 52.7 | |
| | | | | (total yield 21.1) | |

As background information for the yields and recovery of the bark components, the mass balances of the cooking experiments of spruce pulp mill bark are shown in the following Tables 21 and 22.

TABLE 22

Yields of dissolved BL-tannin during soda and kraft cooking and the yields of precipitated BL-tannins on original bark.

| Black liquor from cooking of Spruce pulp mill bark | BL tannin yield in BL based on UV-280 nm, % on bark | BL tannin yield by acidification, % on bark |
|---|---|---|
| Soda cooking, 60 min | 31.8 | 22.7 |
| Soda cooking, 90 min | 29.1 | 25.5 |
| Soda cooking, 120 min | 28.3 | 26.8 |
| Kraft cooking, 60 min | 29.5 | 25.2 |
| Kraft cooking, 90 min | 30.9 | 26.2 |
| Kraft cooking, 120 min | 30.9 | 28.2 |

The glucan yield over cooking is typically 75%, suggesting that about % of the bark glucan is other than cellulose. The polyphenols in the original bark can be recovered from the black liquor by acidification, as a BL tannin fraction, at 60-70% yield, the rest remaining in the black liquor and also in the pulp fraction.

TABLE 21

Composition of spruce bark pulps (starting material), as well as the same bark pulp from soda cooking (SC) and kraft cooking (KC), and pulping yields.

| | Neutral sugars (anhydrocorrected), % | | | | | |
|---|---|---|---|---|---|---|
| | Rhamnose | Arabinose | Galactose | Glucose | Xylose | Mannose |
| Starting material | 0.4 | 3.5 | 2.0 | 27.4 | 3.2 | 4.0 |
| SC, 60 min | 0.1 | 1.3 | 0.9 | 51.9 | 6.4 | 2.2 |
| SC, 90 min | 0.1 | 1.3 | 1.1 | 51.2 | 6.3 | 2.1 |
| SC, 120 min | 0.1 | 1.3 | 0.9 | 49.9 | 6.6 | 2.2 |
| KC, 60 min | 0.1 | 1.2 | 1.0 | 57.9 | 6.5 | 2.6 |
| KC, 90 min | 0.1 | 1.3 | 0.9 | 57.4 | 6.8 | 2.2 |
| KC, 120 min | 0.1 | 1.2 | 0.8 | 58.8 | 6.7 | 2.5 |

| | Neutral sugars (anhydrocorrected), % Fructose | As polysacchar., % | Gravimetric lignin + tannin, % | Soluble lignin + tannin, % | Lignin + tannin, total, % | Cooking yield, % |
|---|---|---|---|---|---|---|
| Starting material | 0.09 | 40.4 | 40.3 | 1.1 | 41.4 | 100.0 |
| SC, 60 min | 0.1 | 63 | 22.8 | 0.2 | 23.0 | 39.5 |
| SC, 90 min | 0.1 | 62 | 22.9 | 0.3 | 23.2 | 38.8 |
| SC, 120 min | 0.1 | 61 | 23.9 | 0.2 | 24.1 | 37.1 |
| KC, 60 min | 0.1 | 69 | 16.3 | 0.2 | 16.5 | 35.6 |
| KC, 90 min | 0.1 | 69 | 15.4 | 0.1 | 15.5 | 34.4 |
| KC, 120 min | 0.1 | 70 | 15.4 | 0.1 | 15.5 | 34.0 |

Example 10—Processing of Pulp as Such

The fiber properties of the bleached pulp were determined (Table 23) for the evaluation of the suitability of the material for reinforcing purposes. No further testing was done in this respect.

TABLE 23

Fiber characteristics of the bleached pulp.

| Fibre distribution, FS5, ISO16065-2 | BLEACHED SODA BARK PULP |
|---|---|
| Arithmetic av. fibre length, mm | 0.54 |
| Length weighted av. fibre length, mm | 0.83 |
| Weight weighted av. fibre length, mm | 1.28 |
| Coarseness, mg/m | 0.084 |
| Fiber curl, % | 22.4 |
| Kink index, 1/m | 3199 |
| Fiber width, µm | 16.9 |
| Vessels, 1/1000 fibers | 13.1 |
| Fibrillation, % | 1.50 |
| Length < 0.2 mm, % | 21.8 |
| Fines A (flake like), % | 21.0 |
| Fines B (lamellar), % | 3.57 |

Example 11—Tannin Solubilization by Alkali-$O_2$ Oxidation

The black liquor tannin fraction obtained as described in Example 2, by cooking in alkali at 160° C. for 90 min, and isolated by adding $H_2SO_4$ to lower the pH to a level of 2.5, was used in the following oxidations.

The acidic, washed bark precipitate rich in tannin (dm. 19.0%) was dissolved in alkali to obtain a solution, which contained 15% of tannin and had pH of 13.4 (T=22° C.). Alkali dose used was 28% of tannin. The alkaline tannin solution was oxidized under oxygen ($O_2$) over pressure in a reactor vessel under efficient gas mixing. During the oxidation, NaOH solution was fed into the reactor to control pH. The reaction was held for 30 min. Two oxidation trials were carried out. During the first trial (TanniOx 1), 30% of NaOH on tannin was fed into the reactor and during the second trial (TanniOx), 15% of NaOH on tannin was used. The $O_2$ consumed during the oxidations, contributed to 17% and 15% of tannin, respectively. The tannin content in the oxidized solutions was measured using UV280 (a=25.78 L/g cm). The oxidized solutions were also determined for molar mass by alkaline SEC and charge by polyelectrolyte titration (Mutek). The results are shown in Table 24.

TABLE 24

Analysis of tannin before and after alkali-$O_2$ oxidation

| | Mn, Da | Mw, Da | Polydispersity | Anionic charge at pH 6, mmol/g | Tannin by UV280, % |
|---|---|---|---|---|---|
| Tannin (washed bark precipitate) | 1544 | 3116 | 2.0 | n.d. * | 19.0 |
| TanniOx 1 | 1834 | 4363 | 2.4 | −5.2 | 13.0 |
| TanniOx 2 | 2391 | 7096 | 3.0 | −4.6 | 13.3 |

* Tannin is not soluble under pH 6.

The above described procedure was carried out on precipitated tannins, redissolved in alkali. However, it is also possible to carry out the oxidations directly on the tannins of the spent cooking liquor.

Example 12—Decrease of Water Surface Tension by Tannin

Surface tension of water (in air atmosphere) was measured as a function of tannin concentration using a Wilhelmy plate tensiometer with a platinum plate (by attention). Different tannin samples and references were used. The origin of the samples was described in Example 11, and the processing methods of the samples are described below.

The samples were dissolved in Borax-NaOH buffer in the given concentration (0.001-100 g/l) to obtain a solution with pH 11. The pH 11 conditions were selected to allow Tannin and Kraft lignin dissolution. In addition, Boric acid-Borax buffer, pH 8 was used to prepare a solution of water soluble, oxidized tannin (TanniOx 2). pH of 11 ja 8 represent, e.g. the pH conditions of alkaline cleaning products that typically contain surface active agents to aid the washing process.

Figure 5:
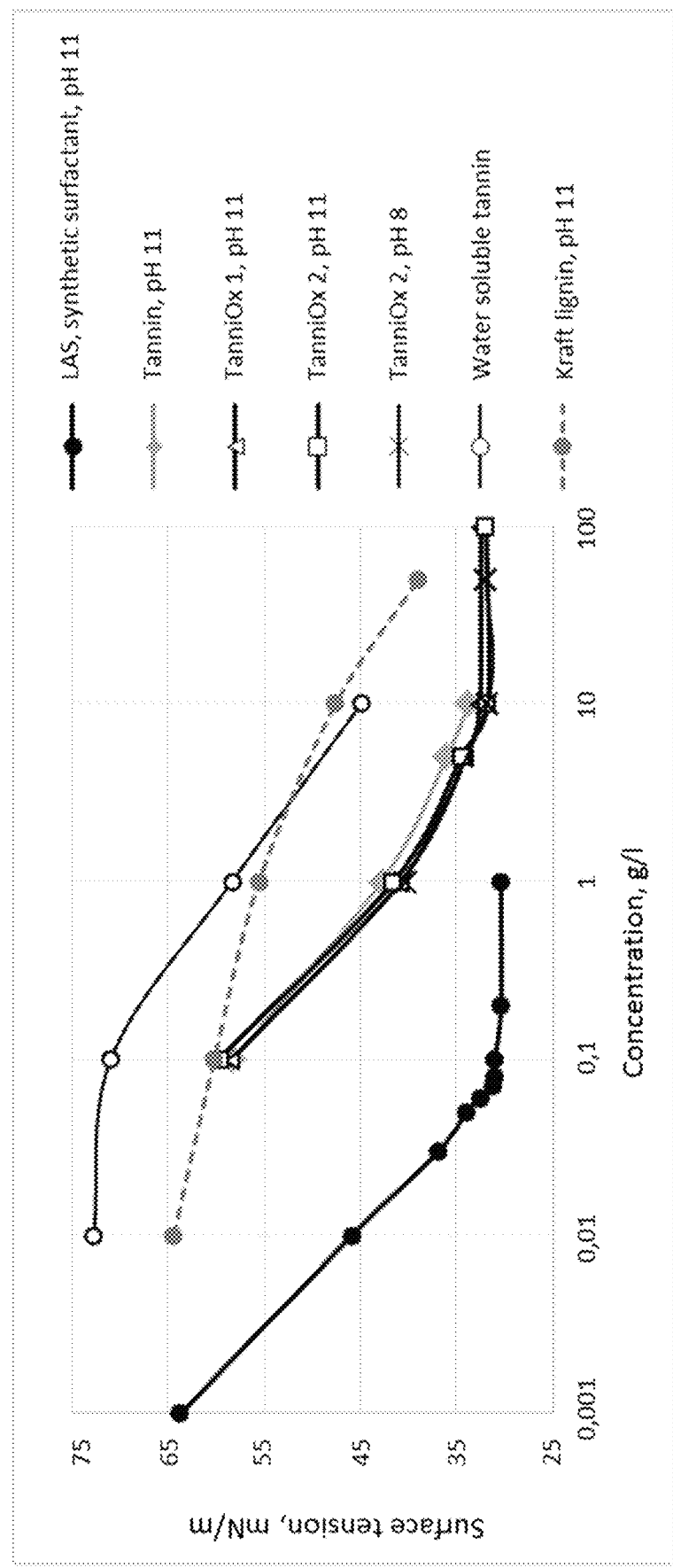
FIG. 5 shows the surface tension of water (pH 11) as a function of precipitated tannin before and after oxidation, by using commercial molecular surfactant (linear alkyl benzenesulfonate, LAS), water soluble tannins, as well as kraft lignin as reference samples.

The results are shown in FIG. 5.

As the results indicate, both the tannin precipitated from soda cooking black liquor and its oxidized form can be used as bio-based polymeric surfactants. However, as the combined results of Examples 11 and 12 demonstrate, oxidation allows the use of tannin in broader pH conditions, e.g. at pH 8 or below.

Tannin and oxidized tannin could find end-use as polymeric surfactants in washing or cleaning product formulations, as well as in many other end-uses requiring polymeric surface active agents. The surface tension decreasing ability of precipitated tannin is clearly better than that of water soluble tannin or kraft lignin.

Example 13—Fibrillation of Bark Pulp

The bark pulp obtained from Example 2 was washed and freezed before fibrillation at 18% solids content. The material was pre-refined by grinding (Masuko): Pass 1:1300 rpm, 0.18 mm gap, pass 2:1300 rpm, 0.14 mm gap, total 2 kWh/kg. Further fibrillation was done at lab scale by microfluidization (M110-EH) at 2% solids content, diluted with deionized water at pH ~9. Fluidization at 2% solids: Pass 1: chambers 400 µm+200 µm, 1000 bar, passes 2-3: chambers 400 µm+100 µm, 1800 bar.

Figure 6:
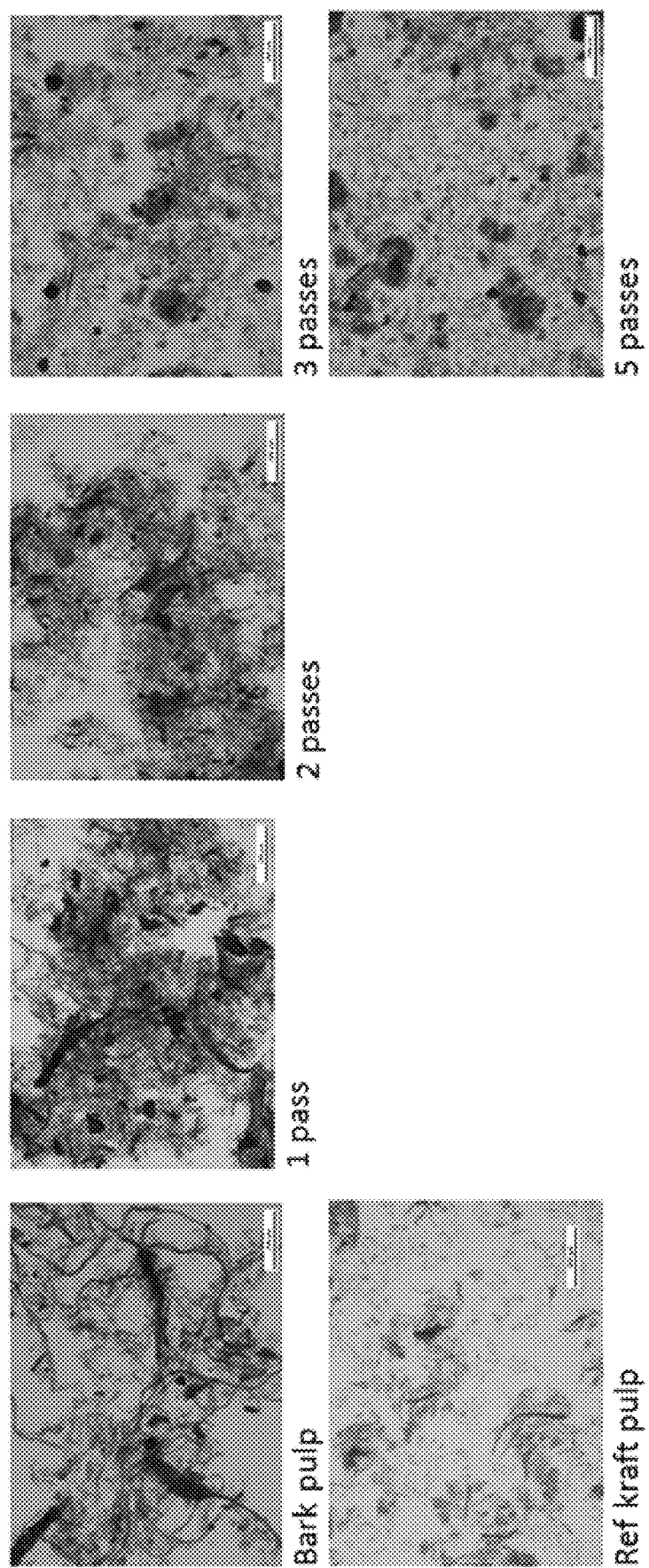
FIG. 6 shows the development of the sample size and shape distribution as a function of the number of passes for bark pulp (up to 3 passes) and reference kraft pulp (up to 5 passes) in the fibrillation of pulp samples.
Figure 7:
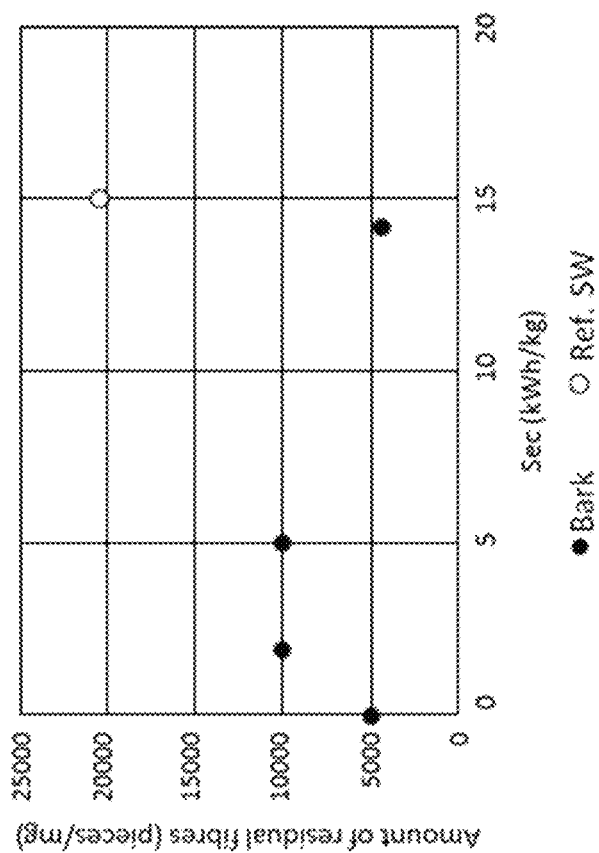
FIG. 7 shows the proportion of fines and micron size residual fibre particles in fibrillated bark samples (ref softwood kraft pulp CNF)
Figure 7:
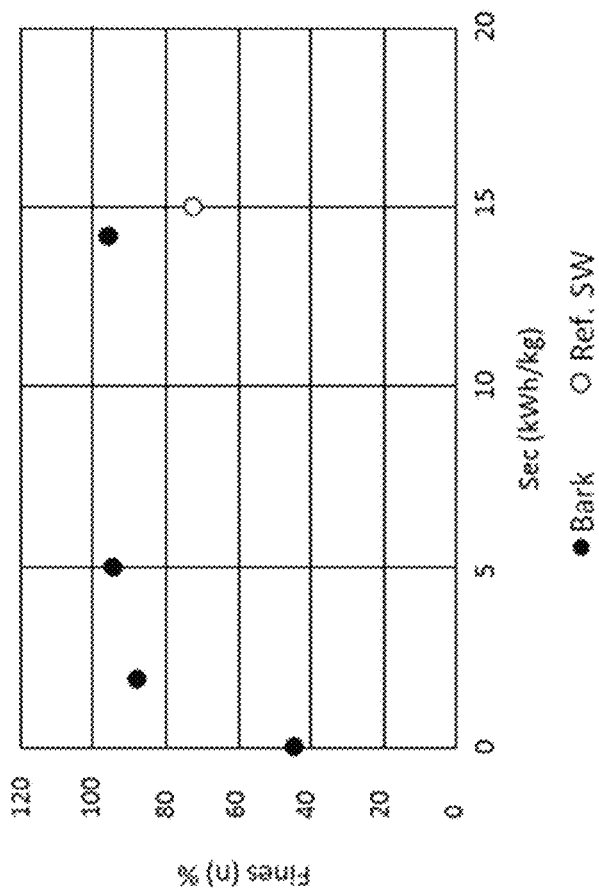

The sample size and shape distribution was rather heterogeneous in the bark samples, as compared to the reference softwood kraft pulp typically used as raw material in CNF production. However, fibrillation produced quite similar CNF products (see FIG. 6). Compared to the SW kraft pulp CNF, the bark pulp CNF was also found to have lower aspect ratio fibres and weaker fibre network, as well as higher content of fines (see FIG. 7), and it was found to have a lower viscosity.

INDUSTRIAL APPLICABILITY

The present material can be used as a means of utilizing further fractions of wood, and generally for applying the conventional cellulose pulping process also on the bark of some commonly utilized wood species.

In particular, the present material is useful in extracting polyphenols, especially tannins, from said bark raw materials.

CITATION LIST

Patent Literature

ES 537060
US 836
U.S. Pat. No. 2,819,295

Non-Patent Literature

Z. Feng and R. Alen, "Selectivity of soda-AQ pulping of kenaf bark", Cellulose Chemistry and Technology 36 (2003) 367-374, M. Kubota, et al., "Use of Karamatsu bark extracts for wood adhesives. VII", Rinsan Shikenjoho 1 (1987) 10-17, Japanese.

M. Ruuskanen, "The influence of the origin and treatment history of spruce and pine bark on the extraction of tannin", Master's thesis, University of Helsinki (May 2017)

The invention claimed is:

1. A process for extraction of valuable components from a tannin-rich bark raw-material, the process comprising: carrying out a pre-treatment on the bark raw material, before an alkaline cooking step, to remove, or at least to decrease the content of silicon and ashes, the pre-treatment comprising washing the bark material with one or more acids or chelating agents at a temperature of 30-50° C., and separating and collecting solids for the alkaline cooking step, and carrying out the alkaline cooking step of the tannin-rich bark raw-material, followed by acid precipitation to provide a solid fraction comprising the valuable components, wherein the alkaline cooking step comprises using a white liquor comprising sodium hydroxide (NaOH) and sodium sulfide ($Na_2S$), thereby obtaining a black liquor comprising polyphenols.

2. The process of claim 1, comprising selecting the bark raw material from the bark or roundwood of softwood species, or from the bark of oak, acacia, willows, chestnut or eucalyptus.

3. The process of claim 1, comprising selecting the bark raw material from the bark of the softwood species pine and spruce.

4. The process of claim 1, further comprising separating the black liquor obtained from the alkaline cooking step from remaining bark pulp.

5. The process of claim 1, comprising applying the following conditions in the alkaline cooking step: 14-20% effective alkali (EA), 150-178° C., and 60-180 min cooking time.

6. The process of claim 5, comprising applying a white liquor with an effective alkali content of 16-18%.

7. The process of claim 5, comprising applying a temperature of 160-170° C. during the alkaline cooking step.

8. The process of claim 5, comprising maintaining the cooking conditions during the alkaline cooking step for 2 or more hours.

9. The process of claim 1, comprising carrying out the acid precipitation by acidifying the black liquor obtained from the alkaline cooking step using sulfuric acid ($H_2SO_4$) at a temperature of 60-90° C., and to a pH level of 2-3.

10. The process of claim 1, further comprising separating the product from the acid precipitation step into a solid fraction containing polyphenolics and a liquid fraction containing cooking chemicals as well as degradation products.

11. The process of claim 1, further comprising carrying out a hot-water extraction (HWE) before the alkaline cooking step, by adding the raw material to an aqueous solution and heating the resulting mixture for 1-5 h at 70-110° C., in order to separate a first portion of the valuable components from the bark raw material.

12. The process of claim 11, wherein the separating of the first portion of the valuable components is done by separating the aqueous solution after the HWE treatment by membrane separation into an organic fraction, containing polyphenolics, and an inorganic fraction.

13. The process of claim 1, further comprising separating the product from the acid precipitation step into a solid fraction comprising a polyphenolic fraction and a liquid fraction containing cooking chemicals as well as degradation products, and processing the solid fraction from the acid precipitation step to give phenolic resins, or alternatively by oxidation to give solubilized tannins.

14. The process of claim 13, wherein the processing of the solid fraction comprising the polyphenolic fraction comprises subjecting the solid fraction comprising the polyphenolic fraction to hydroxymethylation to provide phenolic resins.

15. The process of claim 1, further comprising processing bark pulp remaining after the alkaline cooking step by either enzymatic hydrolysis, to give a glucose hydrolysate, or by bleaching, to give a dissolving pulp.

16. The process of claim 1, wherein the process is done on a bark side stream of a chemical pulping plant, whereby bark is obtained from the debarking of the wood material intended to undergo pulping, and wherein the liquor remaining after the process of claim 1 is returned to a stream of the wood pulping process.

17. The process of claim 1, wherein the valuable components comprise at least tannins and lignin.

18. The process of claim 1, wherein the pre-treatment on the bark raw material further comprises crushing the raw material to obtain a material having a particle size of <5 mm prior to the washing.

19. A process for extraction of valuable components from a tannin-rich bark raw-material, the process comprising:
carrying out a pre-treatment on the bark raw material, before an alkaline cooking step, to remove, or at least to decrease the content of silicon and ashes, the pre-treatment comprising washing the bark material with one or more acids or chelating agents at a temperature of 30-50° C., and separating and collecting solids for the alkaline cooking step, and
carrying out the alkaline cooking step of the tannin-rich bark raw-material, followed by acid precipitation to provide a solid fraction comprising the valuable components, wherein the alkaline cooking step comprises using a white liquor comprising sodium hydroxide (NaOH), thereby obtaining a black liquor comprising polyphenols.

* * * * *